(12) United States Patent  
Ginsburg

(10) Patent No.: US 10,319,468 B2  
(45) Date of Patent: Jun. 11, 2019

(54) MEDICAL SERVICES TRACKING SYSTEM AND METHOD

(71) Applicant: Leonard Ginsburg, Merion, PA (US)

(72) Inventor: Leonard Ginsburg, Merion, PA (US)

(73) Assignee: Leonard Ginsburg, Merion, PA (US)

( * ) Notice: Subject to any disclaimer, the term of this patent is extended or adjusted under 35 U.S.C. 154(b) by 817 days.

(21) Appl. No.: 14/666,278

(22) Filed: Mar. 23, 2015

(65) Prior Publication Data

US 2015/0269323 A1 Sep. 24, 2015

Related U.S. Application Data

(60) Provisional application No. 61/968,693, filed on Mar. 21, 2014.

(51) Int. Cl.
*G16H 10/60* (2018.01)
*G06F 19/00* (2018.01)
*G16H 15/00* (2018.01)

(52) U.S. Cl.
CPC ............ *G16H 10/60* (2018.01); *G06F 19/00* (2013.01); *G16H 15/00* (2018.01)

(58) Field of Classification Search
CPC ........ G06Q 50/22; G06Q 50/24; G06Q 10/10; G06Q 30/04; G06F 19/322; G06F 19/324; G06F 19/327; G06F 19/345; G06F 19/3487; G06F 19/328; G06F 17/243; G16H 10/60; G16H 15/00

See application file for complete search history.

(56) References Cited

U.S. PATENT DOCUMENTS

2006/0064020 A1 3/2006 Burnes et al.
2009/0265188 A1* 10/2009 Lamy .................. G06F 3/04817
705/3

(Continued)

FOREIGN PATENT DOCUMENTS

JP 2017510015 4/2017
WO WO-2015143455 9/2015
WO WO-2018057918 A1 3/2018

OTHER PUBLICATIONS

"U.S. Appl. No. 15/275,223, Preliminary Amendment filed Mar. 16, 2017", 11 pgs.

(Continued)

*Primary Examiner* — Jonathan Durant
(74) *Attorney, Agent, or Firm* — Moser Taboada

(57) ABSTRACT

Some embodiments include a system and computer-implemented method for aggregating and tracking medical delivery to a patient including a non-transitory computer-readable medium in data communication with at least one processor, where the non-transitory computer-readable medium includes software instructions for a medical services tracking system and method. Upon execution of the software instructions, information from a patient database or server can be received and displayed a medical record dashboard. A user can view and edit access to the information, and a user selectable link can display medical record information. The system and method enable auto-population of medical data entry fields based at least one part on at least one claim made or billing signed off by a physician for at least one medical service or procedure previously provided to or performed on at least one patient.

27 Claims, 22 Drawing Sheets

(56) References Cited

U.S. PATENT DOCUMENTS

| | | |
|---|---|---|
| 2010/0057646 A1 | 3/2010 | Martin et al. |
| 2010/0094649 A1* | 4/2010 | White ................... G06F 19/324 705/2 |
| 2011/0004494 A1 | 1/2011 | Denny, Jr. et al. |
| 2011/0202370 A1* | 8/2011 | Green, III ............. G06F 19/328 705/3 |
| 2011/0276348 A1* | 11/2011 | Ahn ....................... G06F 19/328 705/3 |
| 2012/0078664 A1* | 3/2012 | Hasan ................... G06F 19/324 705/3 |
| 2012/0130197 A1 | 5/2012 | Kugler et al. |
| 2013/0024206 A1 | 1/2013 | Hughes et al. |
| 2013/0027411 A1* | 1/2013 | Hebler ................ G06F 19/3418 345/501 |
| 2013/0083185 A1* | 4/2013 | Coleman, III ........... A61B 3/12 348/78 |
| 2013/0191161 A1* | 7/2013 | Churchwell ........... G06Q 50/24 705/3 |
| 2013/0290005 A1* | 10/2013 | Vesto .................... G06Q 50/22 705/2 |
| 2014/0012597 A1 | 1/2014 | Nolte et al. |
| 2014/0074509 A1 | 3/2014 | Rubendran et al. |
| 2014/0236631 A1 | 8/2014 | Perrin et al. |
| 2014/0236635 A1 | 8/2014 | Liberty et al. |
| 2015/0052032 A1* | 2/2015 | Aharoni ................. G06Q 10/00 705/30 |
| 2016/0063212 A1 | 3/2016 | Monier et al. |
| 2016/0198996 A1 | 7/2016 | Dullen |
| 2016/0321404 A1 | 11/2016 | Ginsburg |
| 2017/0116373 A1 | 4/2017 | Ginsburg et al. |

OTHER PUBLICATIONS

"International Application Serial No. PCT/US2015/022091, International Preliminary Report on Patentability dated Sep. 29, 2016", 7 pgs.

"International Application Serial No. PCT/US2015/022091, International Search Report dated Jun. 29, 2015", 3 pgs.

"International Application Serial No. PCT/US2015/022091, Written Opinion dated Jun. 29, 2015", 5 pgs.

"U.S. Appl. No. 15/204,900, Non Final Office Action dated Jan. 9, 2018", 32 pgs.

"International Application Serial No. PCT/US2017/052993, International Search Report dated Dec. 1, 2017", 2 pgs.

"International Application Serial No. PCT/US2017/052993, Written Opinion dated Dec. 1, 2017", 9 pgs.

Placement of Inventor work by MD Office in "EyeNet Extra" distributed as a Supplement to an EyeNet magazine available in Oct. 2014 at the American Academy of Ophthalmology (AAO) 2014 conference Oct. 18-21, 2014.

\* cited by examiner

| OCT | | FA | | ICG | | Photo | | VF | | | Extended Opth | | VA | |
|---|---|---|---|---|---|---|---|---|---|---|---|---|---|---|
| OD | OS | OD | OS | OD | OS | OD | OS | OD | OS | OU | OD | OS | OD | OS |
| | | | | | | | | | | | | | | |
| | | | | | | | | | | | | | | |
| | | | | | | | | | | | | | | |
| | | | | ✓ 885b | ✓ 885a | | | | | | | ✓ 885d | | |
| | | 885c | | | | | | | | | | | | |
| | | | | | | | | | | | | | | |

| | A | B | | C | | | | | D | | E | F | G |
|---|---|---|---|---|---|---|---|---|---|---|---|---|---|
| Patient Name | Exam Date | F/U E&M Appt Code | Additional CPT Code | Diagnosis ICD-9 | Colon polyp 45385 | Colon Bx 45380 | Colon Dx 45378 | Upper GI/Bx 43242 | Upper GI/Dx 43235 | Sigmoid oscopy 45330 | Lab Results | BP Other | Notes | EMR | Mssg. Billing |
| Mr. A | 3.14.15 | | | | | | | | | | | | | | |
| Mr. B | 3.14.15 | | | | | | | | | | | | | | |
| Mr. C | 3.14.15 | | | | | | | | | | | | | | |
| Mr. D | 3.14.15 | | | | | | | | | | | | | | |
| Mr. E | 3.14.15 | | | | | | | | | | | | | | |
| Mr. F | 3.14.15 | | | | | | | | | | | | | | |
| Mr. G | 3.14.15 | | | | | | | | | | | | | | |
| Mr. H | 3.14.15 | | | | | | | | | | | | | | |
| Mr. I | 3.14.15 | | | | | | | | | | | | | | |
| Mr. J | 3.14.15 | | | | | | | | | | | | | | |

Color coded: Green if payment paid, yellow if pending, red if denied

FIG. 12D

| Patient Name | Insurance Coverage | Date of Dx of Diabetes | Patient Age | Patient Weight | Patient Height | Body Mass Index | Initial Presenting HbgA1C | Most Recent HgbA1C | Hypertension | Recent BP | All ICD Diagnosis | Medications | Other | Patient Next Appointment | Patient Contact Information | Notes |
|---|---|---|---|---|---|---|---|---|---|---|---|---|---|---|---|---|
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| ☐ Takes you to patients individual review sheet or can take you anywhere else within chart | | | | | | | | | | | | | | | | ☐ Send a message to the patient about anything or allows a note to be written |

Patient in the Practice or by Physician with X diagnosis, in this example below Diabetes

FIG. 12E

MEDICAL SERVICES TRACKING SYSTEM AND METHOD

RELATED APPLICATIONS

This application claims priority from U.S. Patent Application No. 61/968,693, entitled "PHYSICIAN REVIEW SYSTEM" filed on Mar. 21, 2014, the entire contents of which are incorporated herein by reference.

BACKGROUND

Electronic medical record systems that provide computerized interfaces between medical professionals and staff and patient medical records and services or procedures have the potential to significantly improve and streamline the business of medical care. Using these systems, a medical provider can track the delivery of medical care, access a patients medical records, track billing for services provided, and follow a patient's progress. However, these systems typically include complex interfaces that require users to navigate through multiple layers, folders and/or windows to access even basic patient information.

Medical knowledge is doubling every five years, diagnostic tests and procedures are exploding, and documentation requirements for payments are increasing. Doctors are becoming burdened with documentation and administrative tasks rather than spending their time was medical providers. As a result, they have to turn their back to the patient to input their findings and have to navigate through multiple screens to do so. The potential of medical errors, over ordering or under ordering of diagnostic tests and medical, and other related mistakes occurs because information is missed or buried in the electronic interface of the EMR system. Furthermore, physicians increasingly rely on technicians, assistants and other staff to input information, and with a simple miss click of the mouse or human error, improper documentation can occur. Many current EMR systems require significant administrative overhead, and are prone to user error that can result in a discrepancy between billing, claims and payment for professional services and patient procedures. Much documentation involves non-physician input and client information that is subject to human error or carelessness.

There exists a need for a tool that allows physicians to rapidly detect potential problems, inconsistencies, medical changes, potential billing errors, review diagnostic tests and navigate through the entire patient chart history or access to outside sources, all through this one page quick review "cheat interactive notes" allowing a doctor to provide the best possible care.

SUMMARY

Some embodiments include a system for aggregating and tracking medical delivery to a patient comprising a non-transitory computer-readable medium in data communication with at least one processor, where the non-transitory computer-readable medium includes software instructions comprising a medical services tracking system and method. The system comprises one or more processors configured to execute the software instructions to link to and receive patient related information from at least one patient database or server, and display at least one medical record dashboard comprising information received or derived from the at least one patient database. The system comprises one or more processors configured to execute the software instructions to display patient information within one or more windows of the at least one medical record dashboard, and the one or more windows comprising at least one medical data entry field. The system also comprises one or more processors configured to execute the software instructions to provide a user with view and edit access to the at least one medical data entry field, and where any one of the at least one medical data entry field can comprise a user selectable link to a medical record display. The medical record display includes a user selectable toggle to the at least one medical record dashboard. Further, the system enables auto-population of the at least one medical data entry field based at least one part on at least one claim made or billing signed off by a physician for at least one medical service or procedure previously provided to or performed on at least one patient.

In some embodiments, the one or more processors are configured to dynamically link to at least one electronic medical records system. In some further embodiments, the one or more processors are configured to launch the medical services tracking system and method from a user interface of the electronic medical records system as directed by a user. In some further embodiments, the one or more processors are configured to switch between at least one display generated by the medical services tracking system and method and one or more displays generated by the electronic medical records system.

In some embodiments, the view and edit access comprise providing a user with an option to update or mark at least one medical data field based on at least one medical diagnosis. In some further embodiments, the update or mark comprises an icon illustrating a representation of at least one of a worsening diagnosis, a stable diagnosis, or an improving diagnosis. Further, in some other embodiments, the icon comprises a color or graphical change providing a visual representation of at least one of items billed, items not billed, and tests needing reports or interpretations.

In some further embodiments, the one or more processors are configured to display at least one user-selectable medical record in the medical record display. In some embodiments, the at least one user-selectable medical record comprises a test result or diagnosis. In some embodiments, the at least one test result or diagnosis comprises at least one of optical coherence tomography ("OCT"), or fluorescein angiography ("FA"), and/or indocyanine green chorioangiography ("ICG"), and photographic images of a patient's eyes. In some embodiments, the at least one user-selectable medical record comprises at least one test result or diagnosis from any current procedural terminology code ("CPT code") produced by the American Medical Association or any international classification of disease codes version 9 or version 10 ("ICD code") produced by the World Health Organization.

Some embodiments of the invention include the one or more processors configured to auto-populate the at least one medical data entry field based at least in part on a pending or unbilled medical service or procedure previously provided to or performed on at least one patient. In some embodiments, at least one patient database comprises patient information from a medical provider. In some embodiments, the patient information comprises information received from or derived from a transition of care document or proactive care form. In some further embodiments, the patient information comprises information received from or derived from a direct message.

Some embodiments of the invention include a computer implemented medical services method comprising providing a system for aggregating and tracking delivered medical services to a patient comprising a non-transitory computer-readable medium in data communication with at least one processor, where the non-transitory computer-readable medium includes software instructions comprising a medical services tracking system and method, and one or more processors configured to execute the software instructions to perform the medical services tracking system and method comprising. The method comprises receiving patient related information from at least one patient database or server, and displaying at least one medical record dashboard comprising a displayed convergence of at least one medical service or procedure, at least one claim made or billing signed off by a physician for at least one medical service or procedure, and at least one patient medical record. The method includes displaying patient information within one or more windows of the at least one medical record dashboard, the one or more windows comprising at least one medical data entry field. The method includes providing a user with view and edit access to the at least one medical data entry field, where any one of the at least one medical data entry field can comprise a user selectable link to a medical record display. Further, the medical record display includes a user selectable toggle to the at least one medical record dashboard, and the method includes auto-populating the at least one medical data entry field based at least one part on at least one claim made or billing signed off by a physician for at least one medical service or procedure previously provided to or performed on at least one patient.

In some embodiments, the one or more processors are configured to switch between at least one display generated by the medical services tracking system and method and one or more displays generated by an electronic medical records system. In some embodiments, the view and edit access comprise providing a user with an option to update or mark at least one medical data field based on at least one medical diagnosis. In some embodiments of the method, the update or mark comprises an icon illustrating a representation of at least one of a worsening diagnosis, a stable diagnosis, or an improving diagnosis. Further, in some embodiments of the method, the icon comprises a color or graphical change providing a visual representation of at least one of items billed, items not billed, and tests needing reports or interpretations.

In some further embodiments of the method, the one or more processors are configured to display at least one user-selectable medical record in the medical record display. Some embodiments of the method further comprise one or more processors configured to auto-populate the at least one medical data entry field based at least in part on a pending or unbilled medical service or procedure previously provided to or performed on at least one patient.

In some embodiments of the method, the at least one patient database comprises patient information from a medical provider. In some further embodiments, the patient information comprises information received from or derived from at least one of a transition of care document, a proactive care form, and a direct message.

DESCRIPTION OF THE DRAWINGS

FIG. 2 illustrates a medical record window of the medical record system useful for deploying or launching embodiments of the invention described herein.

FIG. 4A illustrates a medical record dashboard in accordance with some embodiments of the invention.

FIG. 4D illustrates a portion of the medical record dashboard of FIG. 4A in accordance with some embodiments of the invention.

FIG. 5A depicts a medical summary update process in accordance with some embodiments of the invention.

FIG. 5B illustrates a notes update process in accordance with some embodiments of the invention.

FIG. 6 illustrates a user action record access process in accordance with some embodiments of the invention.

FIG. 8 illustrates a medical record and diagnosis update process in accordance with some embodiments of the invention.

FIG. 10B illustrates a medical record update marker process in accordance with some embodiments of the invention.

FIG. 11 illustrates a portion of the medical record dashboard of FIG. 4A including a scrolled display in accordance with some embodiments of the invention.

FIG. 12A illustrates a portion of the medical record dashboard in accordance with another embodiment of the invention.

FIG. 12C illustrates a portion of the medical record dashboard of FIG. 12A in accordance with some embodiments of the invention.

FIG. 12D illustrates a portion of a medical record dashboard for display as a function of patients seen during a certain period of time with CPT codes performed in accordance with some embodiments of the invention.

FIG. 12E illustrates a portion of a medical record dashboard for display as a function of patients with a specific disease ICD in accordance with some embodiments of the invention.

DETAILED DESCRIPTION

Figure 1:
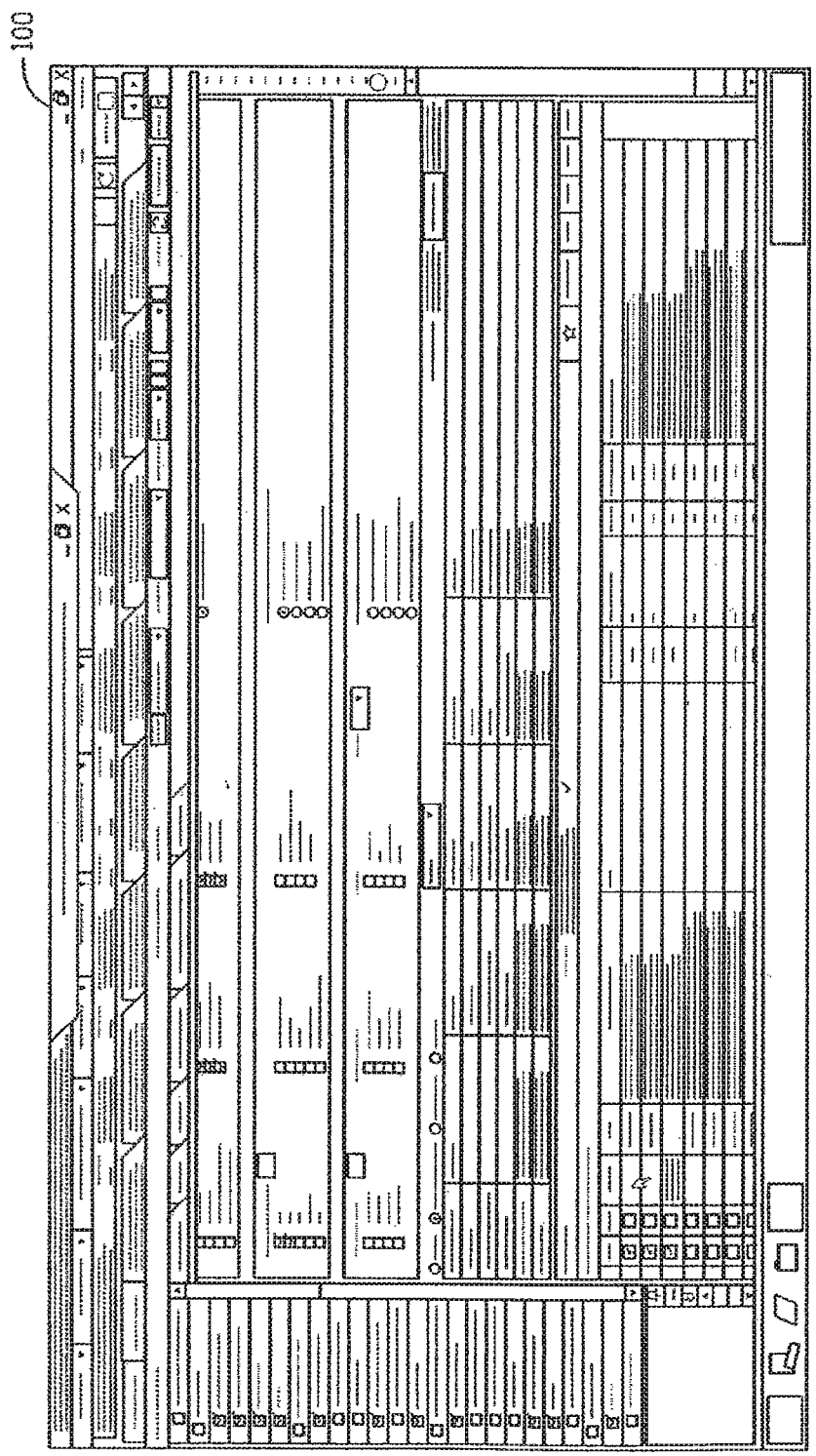
FIG. 1 illustrates a sample medical record system useful for deploying or launching embodiments of the invention described herein.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

Some computerized or electronic medical record ("EMR") systems provide a computerized interface between medical professionals and staff and one or more medical records databases. Some embodiments of the invention disclosed herein include a medical service tracking system and method that can be linked to or otherwise accessed from a conventional EMR system. Examples of such conventional EMR systems include the MD Office medical records and practice management systems distributed by MD Office, Inc. USA, 1967 Oak Tree Road, Edison, N.J., 08820, USA.

Some embodiments of the invention include a medical service tracking system and method that can be included as an add-on software package to a conventional medical record system such as the aforementioned MD Office medical record systems. In some embodiments, tasks associated with an add-on software program can be seamlessly linked and/or incorporated into one or more core software tasks or modules of the conventional medical record system such as MD Office. In some embodiments, application programming interfaces (hereinafter "APIs") can be used to connect and transmit data between one or more software modules of the medical service tracking system and method, and one or more conventional medical record system such as MD Office and/or one or more patient records and/or databases comprising patient records. For example, in some embodiments of the invention, the medical services tracking system and method can be configured to receive patient data from a master patient index or a medical provider.

In some embodiments, new software features of the medical service tracking system and method can be added to an existing application such as MD Office without modifying the existing code of the application. In some other embodiments, the medical service tracking system and method can function as an independent application, not linked, overlaid, or otherwise interfaced with any conventional medical record system such as MD Office.

Figure 2:
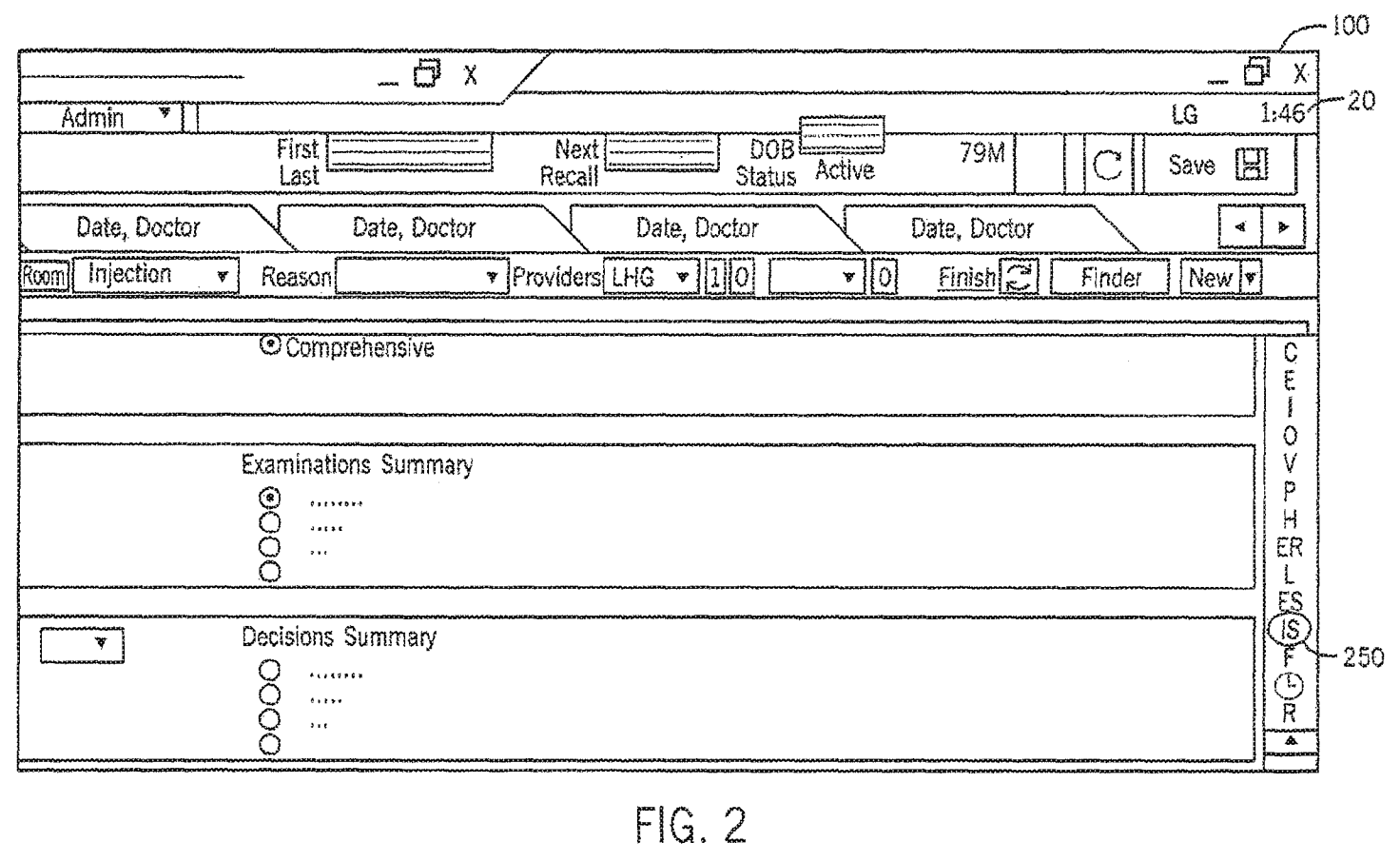

FIG. 1 illustrates sample medical record system 100 useful for deploying or launching embodiments of the invention described herein. In some embodiments, a user, such a medical practitioner, can utilize a conventional medical record system 100 such as MD Office or another medical record system to launch or enter a medical services tracking system. FIG. 2 illustrates a medical record window 200 of the medical record system 100 useful for deploying or launching embodiments of the invention described herein. In some embodiments, the medical record window 200 of a conventional medical record system can include a medical tracking system launch icon 250 to facilitate access to and/or launch of one or more embodiments of the medical service tracking system and method.

In some embodiments, a user can use the medical tracking system launch icon 250 to exit the medical record system 100 with the intent of accessing or launching the medical service tracking system and method. In some further embodiments, the launch icon 250 can be used to temporarily halt the medical record system 100 and access or launch the medical service tracking system and method. In some other embodiments, the launch icon 250 can be used to access or launch the medical service tracking system and method while the medical record system 100 continues to run in parallel, continues to run in a background mode, and/or is moved to an idle mode.

Figure 3:
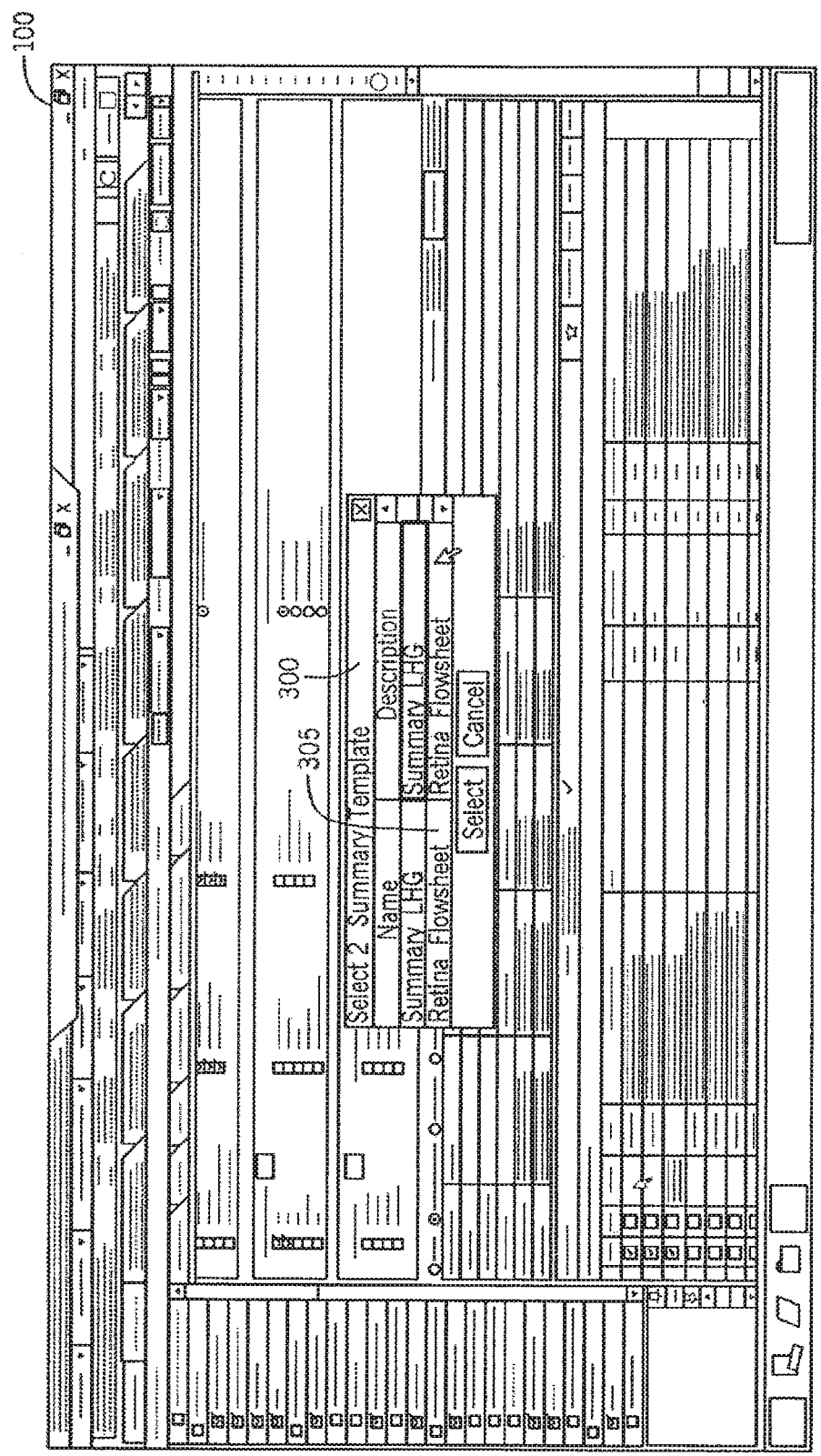
FIG. 3 illustrates a medical record dashboard selection window useful for selecting and launching embodiments of the invention described herein.

Referring to FIG. 3, illustrating a medical record dashboard selection window useful for selecting and launching embodiments of the invention described herein, in some embodiments, after a user selects or clicks the launch icon 250, a medical record dashboard selection window 300 can be displayed. The medical record dashboard selection window 300 can include one or more selectable medical record dashboards from which a user can select to access at least one medical record dashboard. For example, in some embodiments, the user can select "Retina Flowsheet" 305 to access and/or launch a medical record dashboard including a retina flowsheet.

Figure 4A:
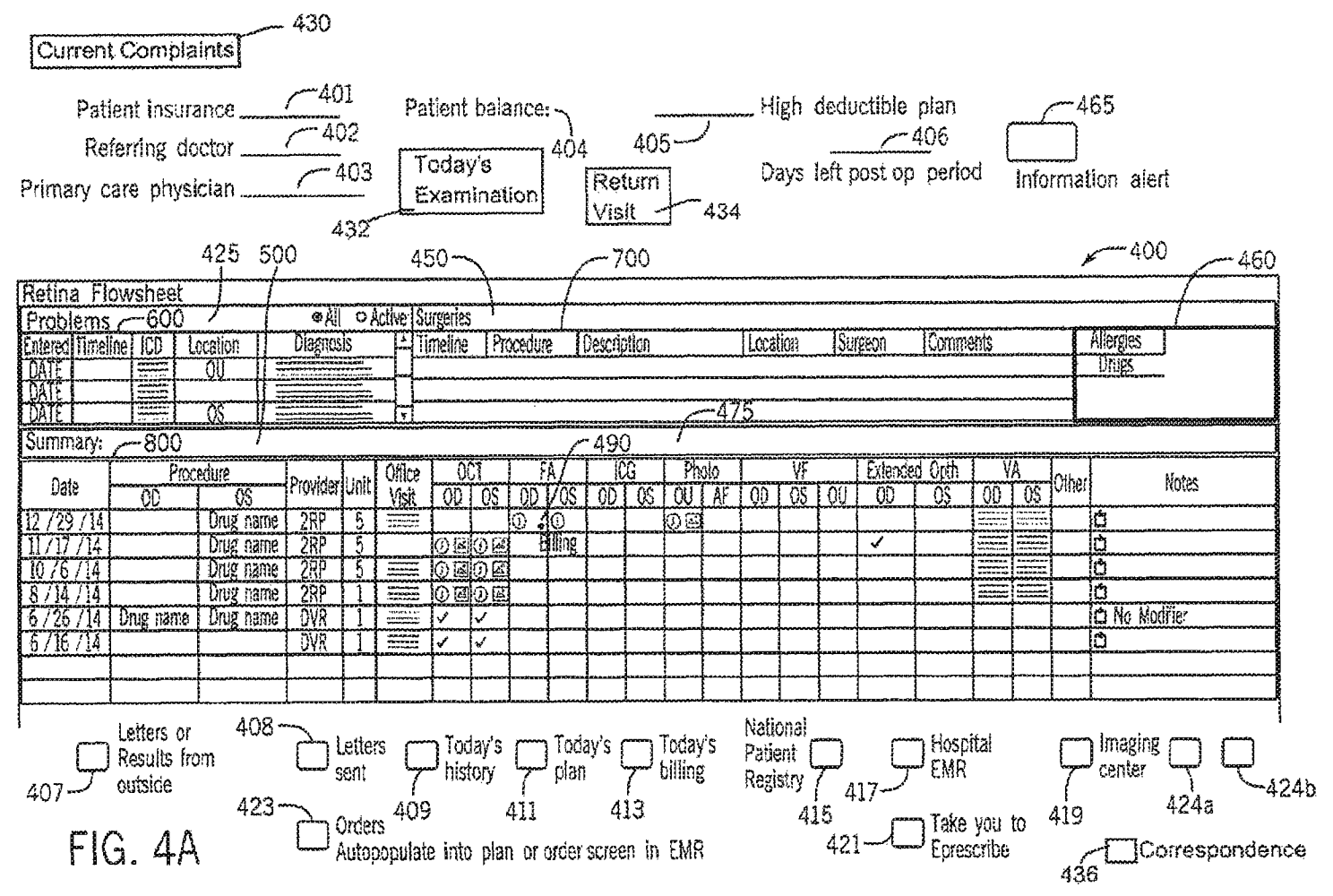

FIG. 4A illustrates a medical record dashboard 400 in accordance with some embodiments of the invention. In some embodiments, the medical record dashboard 400 can be displayed by the user following the user's selection of at least one medical record dashboard from the medical record dashboard selection window 300. In some embodiments, the medical record dashboard 400 can display data from one or more medical records, and/or track medical procedures and services based on claims made or billing signed off by a physician for one or more delivered medical procedures or services. Some embodiments of the invention include a medical service tracking system and method that can dynamically link to various external databases comprising patient information that can be displayed in the medical record dashboard 400. For example, in some embodiments, the medical service tracking system and method can function as a portal to patient information prepared by the user or patient information from other sources. Further, in some embodiments of the invention, the medical record dashboard 400 can be auto-populated as a function of claims made or billing signed off by a physician. In this instance, any data displayed within the medical record dashboard 400 is derived from one or more claim records that have been billed for one or more procedures or services have previously been provided to the patient. In some other embodiments, auto-population can be enabled in both directions interacting as a switchboard between the entire EMR and the medical record dashboard 400 along with what is added to any window, sub-window, column or entry in the medical record dashboard 400 being automatically added to the appropriate part of the chart for documentation. In some embodiments, the medical record dashboard 400 can display information related to medical procedures or services in relation to retinal eye care of a patient. In other embodiments, the medical record dashboard 400 can display information related to medical procedures or services in relation to any kind of medical care of a patient.

In some embodiments, the medical record dashboard 400 can display various windows and sub-windows based on a user preference and/or current or previous user interaction with the medical record dashboard 400. For example, in some embodiments, the medical record dashboard 400 can display a problems window 425 and/or a surgeries window 450 where information related to a patient's medical problems and surgeries can be displayed in information columns 600, 700 respectively. Further, in some embodiments, patient information related to a allergies and drugs can be displayed within the allergies/drug section 460. This information can be auto-populated from a variety of sources, or inputted by personnel. In some embodiments, the medical record dashboard 400 can include a summary window 475 enabling a user to view and edit summary information related to the patient, any details of care provided to the patient, and/or and any medical diagnosis information prepared by a medical practitioner. Further, the medical record dashboard 400 can also display detailed information related to any medical procedures or services provided to the patient, including procedures or services that are auto-populated by claims made, or billings or payments including billing signed off by a physician as detailed above. For example, in some embodiments, the medical record dashboard 400 can display a medical tracking display window 500 including information columns 800 that can be auto-populated by claims made or billings signed off by a physician. The auto-population can include billings, payments, or other information from anywhere in the EMR chart.

The medical record dashboard 400 can include miscellaneous information identifying the patient, information related to the patient's insurance plan, doctors and referring doctors, and the patient's current balance. Other information can relate to the patient's prior visit, prior diagnosis or procedure and any important information relevant to the next visit. Additional information can relate to the current visit, including history of illness and chief medical complaint, billing information, and retrievable medical information including pharmacy information. For example, in some embodiments, the medical record dashboard 400 can include a patient insurance entry 401, referring doctor entry 402, and primary care physician entry 403. The medical record dashboard 400 can also include patient balance entry 404, and a high deductible plan entry 405. Important patient information related to a pending or current visit can include a "days left post op period" entry 406 and/or an information alert 465. In some embodiments, the information alert 465 can be auto-populated based on other information or entries in the medical record dashboard 400. In other embodiments, the information alert 465 can be set by any user to alert the user or other user of information relevant to the patient. In some embodiments, the information alert 465 can comprise a daily technician update, including information to medical information such as blood pressure, or whether the patient is pregnant, or any other urgent information with which a member of a health care team can alert another member. Further, this information can become permanent or can be deleted from the dashboard 400, and from any record or table accessible from the dashboard 400, including any medical record. Further, this information can serve as or be configured as a "sticky note" that can be removed from any of the above-mentioned records. For example, the "sticky note" can be an electronic sticky note riding on the dashboard or any record accessible from the dashboard, or a physical sticky note attached to a physical record, chart or table. Also this table 400 is unique in that test interpretations and evaluation of patients, once documented and billed, usually become date stamped and cannot be easily amended without putting the new date of amendment on it. This table is a medical tool to improve and follow care as such, may not necessarily be used as part of a particular days medical record. Therefore months or years a part doctors can add notes into the table when new findings, discoveries, or realizations warrant it without feeling encumbered that they are "changing past medical record" and a disclosure of such can be at the bottom of the table.

In some other embodiments, a daily technician update can be accessed or otherwise made visible to the user in at least one other portion of the dashboard 400. In some embodiments, the information alert 465 can be displayed in a specific color and/or with a specific graphic and/or animation. For example, in some embodiments, the information alert 465 can comprise a flashing red animation. Also this table 400 is unique in that interpretations and evaluations of patients once documented and billed usually become date stamped and cannot be easily amended without putting the new date of amendment on it. This embodiment of the table is a tool to improve and follow care and as such, may not necessarily be used as part of a particular day's medical record. Therefore months or years apart Doctors can put notes into the table if findings or new discoveries or realizations warrant it, without feeling encumbered that they're changing a past medical record." To protect the physician during an audit a statement on the table can be added that "notes on this table" are not necessarily added at the time listed as the date.

Some embodiments include an alert or access to one or more letters or results from outside (icon 407) systems or third parties. Some further embodiments include an alert or access to letters sent 408. The letters can be written, typed, and/or one or more dictated letters from the user and/or another medical provider.

Some embodiments include an entry or access to the current day's history, the current day's plan, and/or to the current day's billing. For example, some embodiments include a "Today's history" entry or access 409, a "Today's plan" entry or access 411, and a "Todays billing" entry or access 413.

In some embodiments, the medical record dashboard 400 can also include at least one link to information from external databases, providers, hospitals (e.g., such as a discharge summary), clinics and/or testing laboratories, etc., (e.g., where the information can include the overall diagnostic imaging center of the practice for certain pieces of equipment and into the machine to actually see all of the study). In the latter example, the medical record dashboard 400 can receive information from at least one database and/or server and/or controller coupled to receive data from the diagnostic equipment. Further, some embodiments include an entry or access to the National Patient Registry or other kind of registry (link 415), hospital EMR (link 417), imaging center 419 (including accessing software imaging and diagnostic management systems to handle many diagnostic images and studies or specific diagnostic equipment), and Eprescribe link 421.

In some embodiments, the user can access at least one Eprescribe database, server, and/or website directly from the dashboard 400 using the Eprescribe link 421. Further, in some embodiments, orders can be auto-populated into the plan or order screen of EMR ("Orders" link 423).

In some embodiments, one button entitled "clinical research study diagnostic equipment" (button 424a) can take a user (e.g., a physician) instantly to the piece or pieces of equipment that were used that or another day for testing so the doctor can now measure and enter the findings. This can be internal in the user's practice so that any diagnostic equipment can be accessed. In some embodiments, the same or another button can provide a link in the major table to an image or diagnostic management software system. In this way, some embodiments can handle the tremendous amount of diagnostic equipment and images, and unlike prior art tables that just provide access to a PDF, these embodiments provide access to not just one single piece of diagnostic equipment but all of them and the complete study, not just a "slice", can be evaluated and comparison of changes over time made.

Once entered, the data can be auto populated into the dashboard 400 (e.g., such as a retina flowsheet) under other column 1200, where each clinical research study would have other factors followed such as central macular thickness ("CMT"), or ischemic index ("ISI"). Further, the second button (button 424b) can take the user to either the company sponsoring the clinical research website (sometimes a pharmaceutical company and other times a company that invented a device). The clinical researcher could immediately go to this website and input any data that was obtained from that visit from the diagnostic equipment button 424a, and/or to a research spreadsheet where the user (e.g., a clinical researcher in this example embodiments) can input the data, or where the data can be auto-populated (e.g., from the other column 1200 or into column 1200).

Figure 4B:
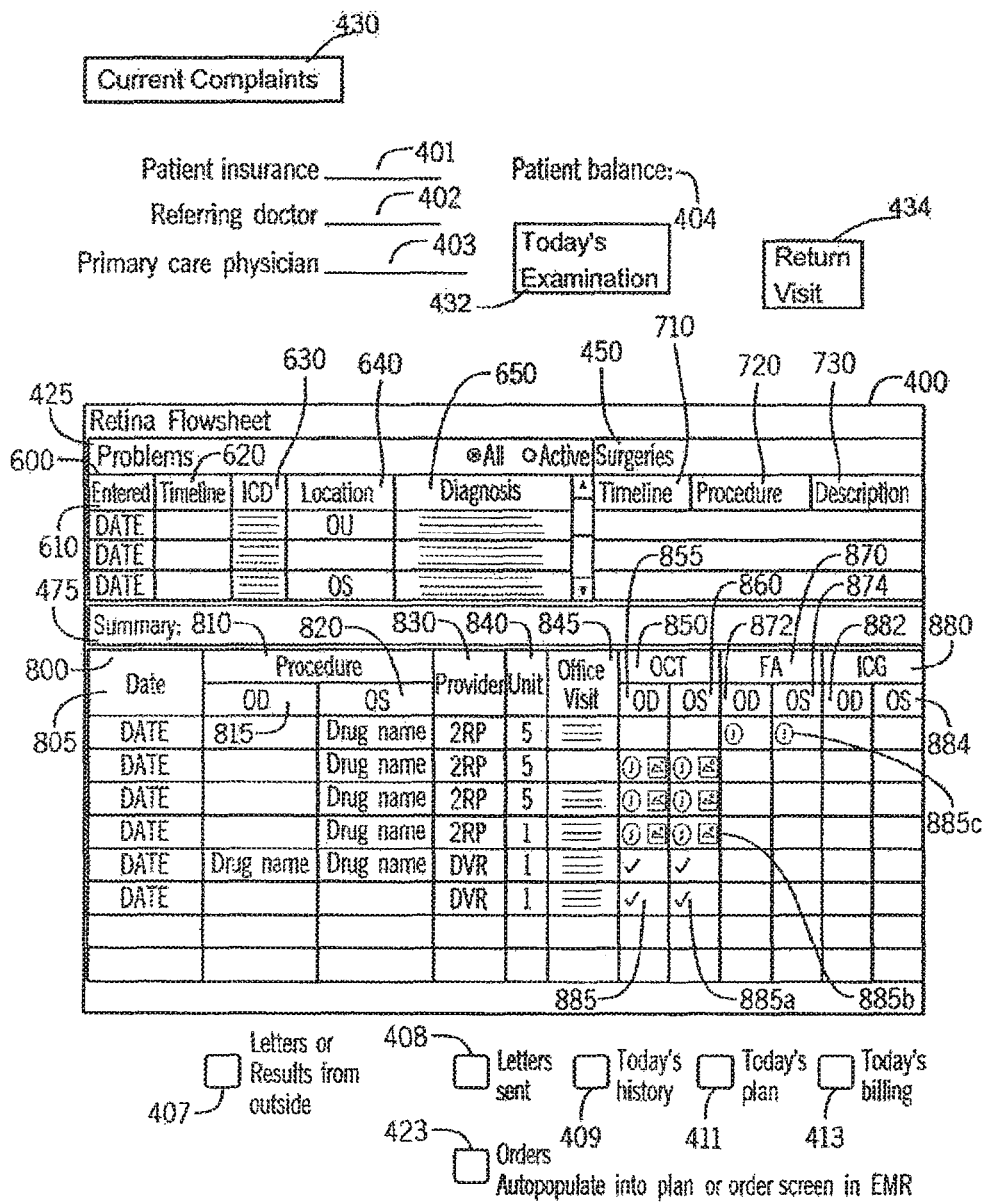
FIG. 4B illustrates a portion of the medical record dashboard of FIG. 4A in accordance with some embodiments of the invention.
Figure 4C:
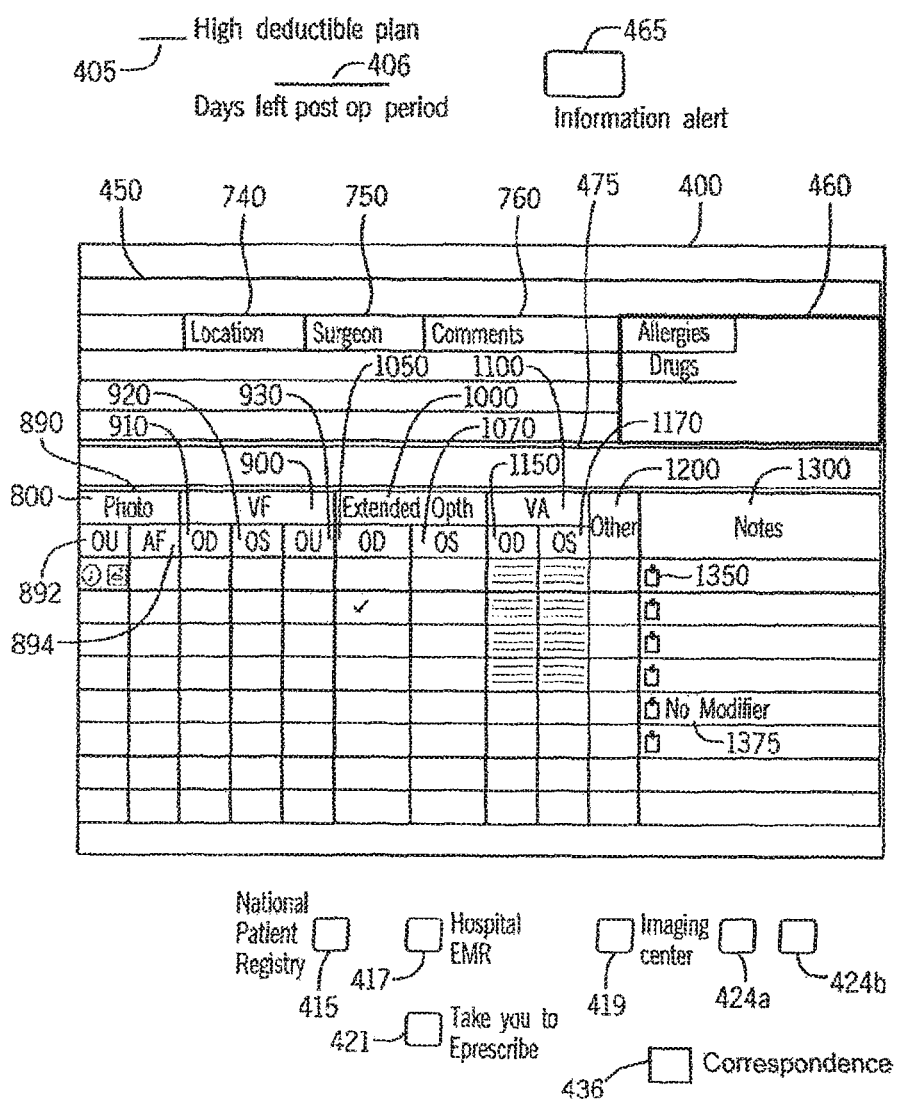
FIG. 4C illustrates a portion of the medical record dashboard of FIG. 4A in accordance with some embodiments of the invention.

Further details of the problems window 425, surgeries window 450, and medical tracking display window 500 and are provided in FIGS. 4B-4D illustrating enlarged views of portions of the medical record dashboard 400. For example, FIG. 4B illustrates a portion of the medical record dashboard of FIG. 4A in accordance with some embodiments of the invention. As illustrated, the information columns 600 of the problems window 425 can include a date and time information in entered date column 610, a timeline column 620, an "ICD" column 630 for international classification of disease codes including international classification of disease codes version 9 or version 10 (hereinafter collectively referred to as "ICD code") information, location of the problem or disorder (shown as "OD", "OS", "OU" identifying right eye, left eye, both eyes), or from any part of the body, and a diagnosis column 650 for detailing information related to an initial diagnosis or final diagnosis of a patients problem or disorder that can be auto-populated or inputted. Further, the information columns 700 of the surgeries window 450 can include information related to services or procedures were provided to the patient (procedure columns 720), a description of the services or procedures performed (description columns 730), and when the services or procedures were provided (timeline columns 710). Referring to FIG. 4C, in some embodiments of the invention, the surgeries window 450 can include location information 740, surgeon or doctor information 750, and a comments section 760.

Referring to the medical tracking display window 500, the information columns 800 can include a date column 805, and a procedure column 810 illustrating or providing access to information detailing one or more procedures performed on the patient. Further, the procedure column 810 can include an "OD" column 815, and "OS" column 820 providing right and left eye procedure information, or could be a body part (i.e., orthopedic surgery limb versus spine). In some embodiments, information related to the medical provider, the location where the procedure was performed, and office visit information can be provided to the user in the provider column 830, and unit column 840, and office visit column 845.

In some embodiments of the invention, the user can view information related to tests and procedures performed on the patient. For example, these can include information related to one or more medical imaging procedures such as an optical coherence tomography ("OCT"), or fluorescein angiography ("FA"), and/or indocyanine green chorioangiography ("ICG"), or any current procedural terminology code (hereinafter "CPT code"), including any CPT code found in the American Medical Association CPT 2015 professional edition, the entire contents of which is incorporated by reference. Moreover, the user can view information related to tests and procedures performed on the patient based on an ICD code.

In some embodiments, medical procedures performed (including any of the aforementioned medical imaging procedures) that have been billed and claimed can be viewed or accessed by a user within any of the "OCT" column 850 (split as an "OD" column 855 and "OS" column 860), an "FA" column 870 (split as an "OD" column 872 and "OS" column 874), and/or "ICG" column 880 (split as "OD" column 882 and "OS" column 884).

Referring to FIG. 4C, illustrating a portion of the medical record dashboard of FIG. 4A in accordance with some embodiments of the invention, the information columns 800 can include a photo column 890 configured to enable a user to access any photographic images of the patients eyes including optical and auto-fluorescent images of the eyes ("OU" column 892 and "AF" column 894). In some embodiments, if visual function tests were performed, information can be viewed or accessed in the "VF" column 900 (including an "OD" column 910, "OS" column 920, and/or "OU" column 930). Some embodiments also include an extended ophthalmology column 1000 (including "OD" column 1050 and "OS" column 1070), and a visual acuity column ("VA" column 1100, including "OD" column 1150, and "OS" column 1170). In some embodiments, as described earlier, other details of various tests, procedures or services can be viewed or accessed in the other column 1200. Further, information associated with any of the user-accessible tests, procedures or services or other notes provided by the user and/or medical provider can be viewed or accessed in the notes column 1300 using one or more notes access icon 1350 and/or by viewing a note entry 1375 (e.g., and/or any note entered using the note entry window 1305). The information can also be auto-populated into the EMR plan pages.

Some embodiments of the invention include visual cues, icons, or markers representing and/or enabling access to detailed information related to medical services, procedures or tests provided to the patient. For example, in some embodiments, medical services, procedures or tests performed or provided can be assigned a visual code, icon, or graphical marker. For example, FIG. 4B at least shows visual cues, icons, or markers 885 representing medical services, procedures or tests performed or provided to the patient. In some embodiments, the information columns 800 within the medical tracking display window 500 can include at least one "test done, no image attached" icon 885a, one or more "see image in order viewer" icon 885b, at least one "view order interpretation" icon 885*c*, and/or at least one "procedure billed or claims made" icon 885*d*, where an appearance in the medical record dashboard 400 represents a claim was made, and a change in color or other method (italics, bold, etc. can represent whether the bill was paid. Further, FIG. 4D illustrates another portion of the medical record dashboard 400 of FIG. 4A in accordance with some embodiments of the invention and shows example of "test done, no image attached" icon 885*a*, "see image in order viewer" icon 885*b*, "view order interpretation" icon 885*c*, and "procedure billed or claims made" icon 885*d*, where an appearance in the medical record dashboard 400 represents a claim was made, and a change in color or other notification method can represent whether the bill was paid.

Figure 5A:
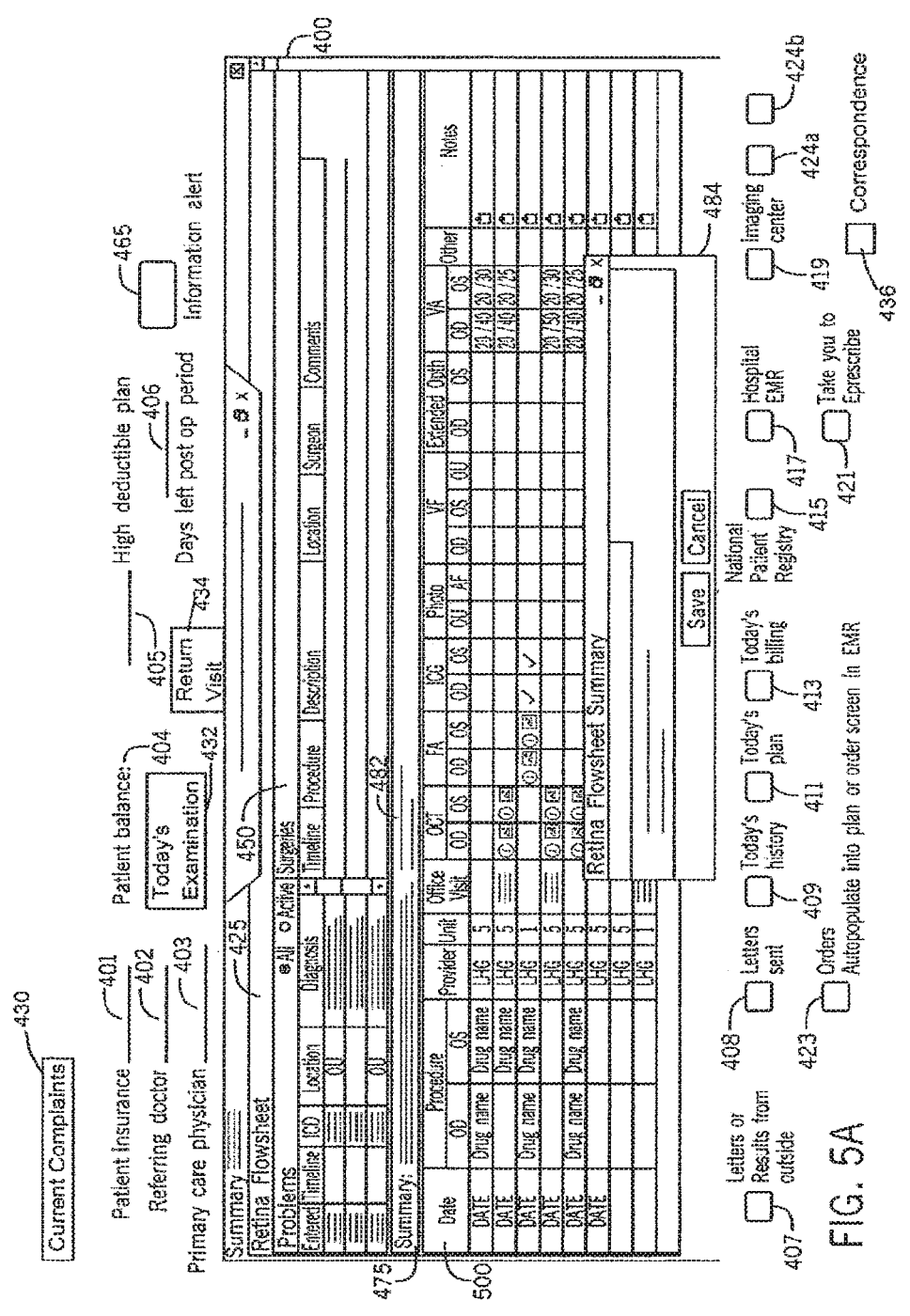

In some embodiments of the invention, the medical record dashboard 400 can provide a text summary of any aspect of the medical record dashboard 400. As described earlier, the summary window 475 can enable a user to view and edit summary information related to the patient, any details of care provided to the patient, and/or and any medical diagnosis information prepared by a medical practitioner. In some embodiments, the user can add and/or edit the summary information. For example, FIG. 5A depicts a medical summary update process in accordance with some embodiments of the invention. In some embodiments, the medical record dashboard 400 including the problems window 425, surgeries window 450, summary window 475, and medical tracking display window 500 can include summary comments 482 that can be entered, updated, expanded using the summary input window 484. In some embodiments, a user can enter information within the summary input window 484 for entry into the summary window 475.

Figure 5B:
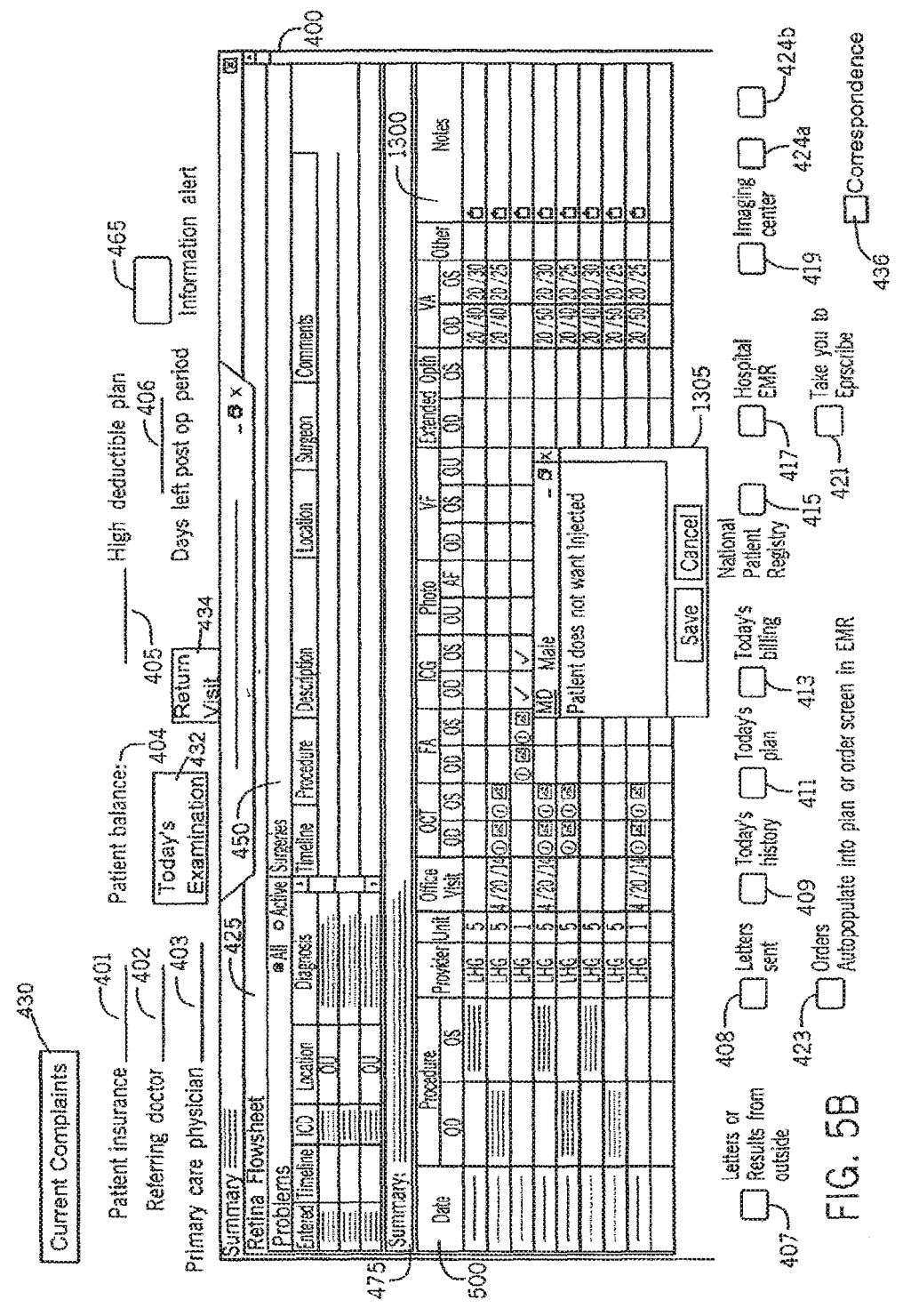

In some embodiments of the invention, the user can add or update information associated with any of the user-accessible tests, procedures or services or other notes provided by the user and/or medical provider in the notes column 1300. For example, FIG. 5B illustrates a notes update process in accordance with some embodiments of the invention. In some embodiments, the medical record dashboard 400 comprising the problems window 425, surgeries window 450, summary window 475, and the medical tracking display window 500 with notes column 1300 can be updated with one or more notes using the note entry window 1305. In some embodiments, placement or viewing functions can be toggled using a left or right mouse click function. For example, in some embodiments, following an initial impression or diagnosis, a right click can be updated or shown in a note (e.g., through note entry window 1305), and/or a left click can show in the summary (e.g., summary window 475 as summary comments 482). Further, a right-click for instance or other method can insert what is typed in the table into the corresponding area of the medical chart (e.g., the plan), whereas a left click would insert only into the table and not any other location within the EMR.

Figure 6:
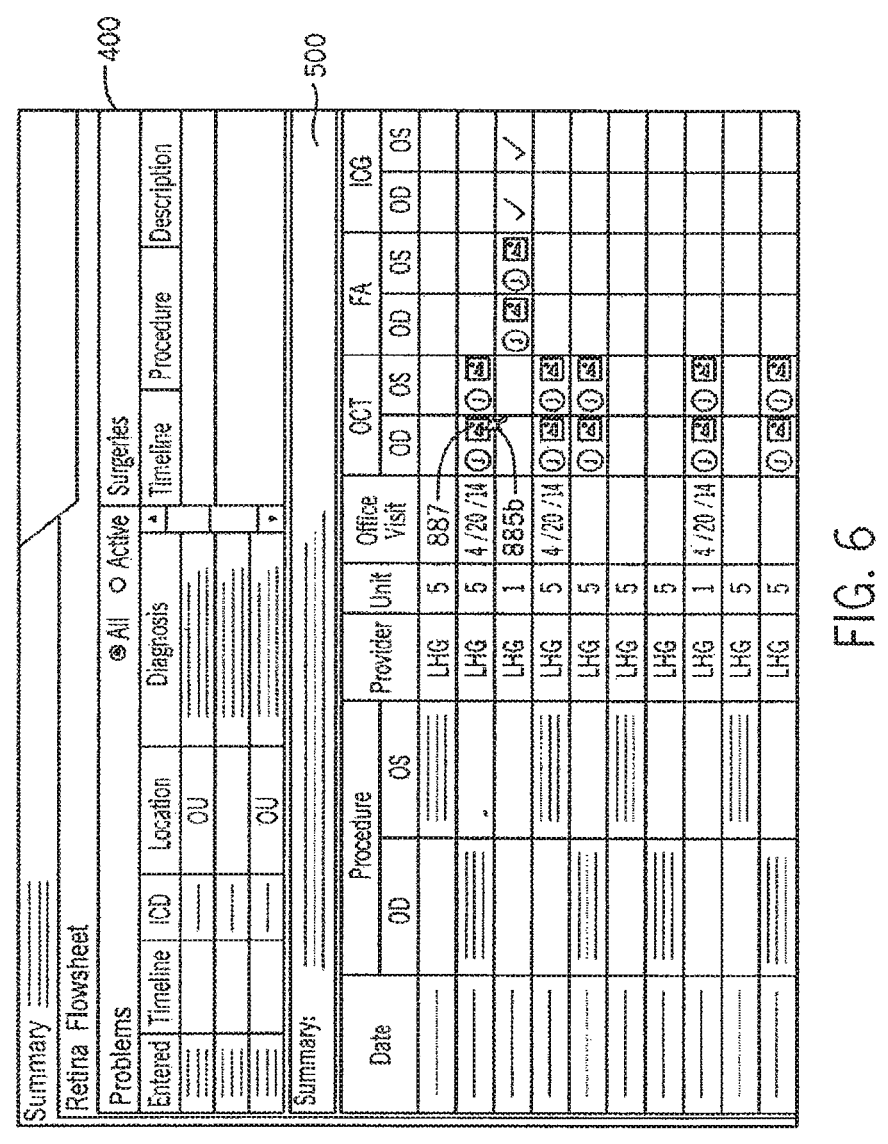

Regarding the visual cues, icons, or markers 885 (referred to above and shown at least in FIG. 4B), in some embodiments, a user can access underlying information linked to the visual cues, icons, or markers 885. For example, using a single click or mouse-over, a user can use the medical tracking display window 500 of the medical record dashboard 400 to access and view any information auto-populated within the medical tracking display window 500 and/or other windows or sub-windows of the medical record dashboard 400. For example, FIG. 6 illustrates a user action record access process in accordance with some embodiments of the invention. In some embodiments, a user action 887 (depicting a user click or mouse-over of a cursor) can enable a user to access and view information (in this example, information lined to "see image in order viewer" icon 885*b*). In some further embodiments, a user can use a single click or mouse-over to user can access and view any information within any portion of the medical record dashboard 400. Further, in some embodiments, a user can use left and right mouse clicks to navigate from one portion of the medical record dashboard 400 to another. Furthermore, in some embodiments, a right-click mouse function update the user and/or display any important information in the medical record dashboard 400, and a left-click can bring the user back to another portion of the medical record dashboard 400.

Figure 7:
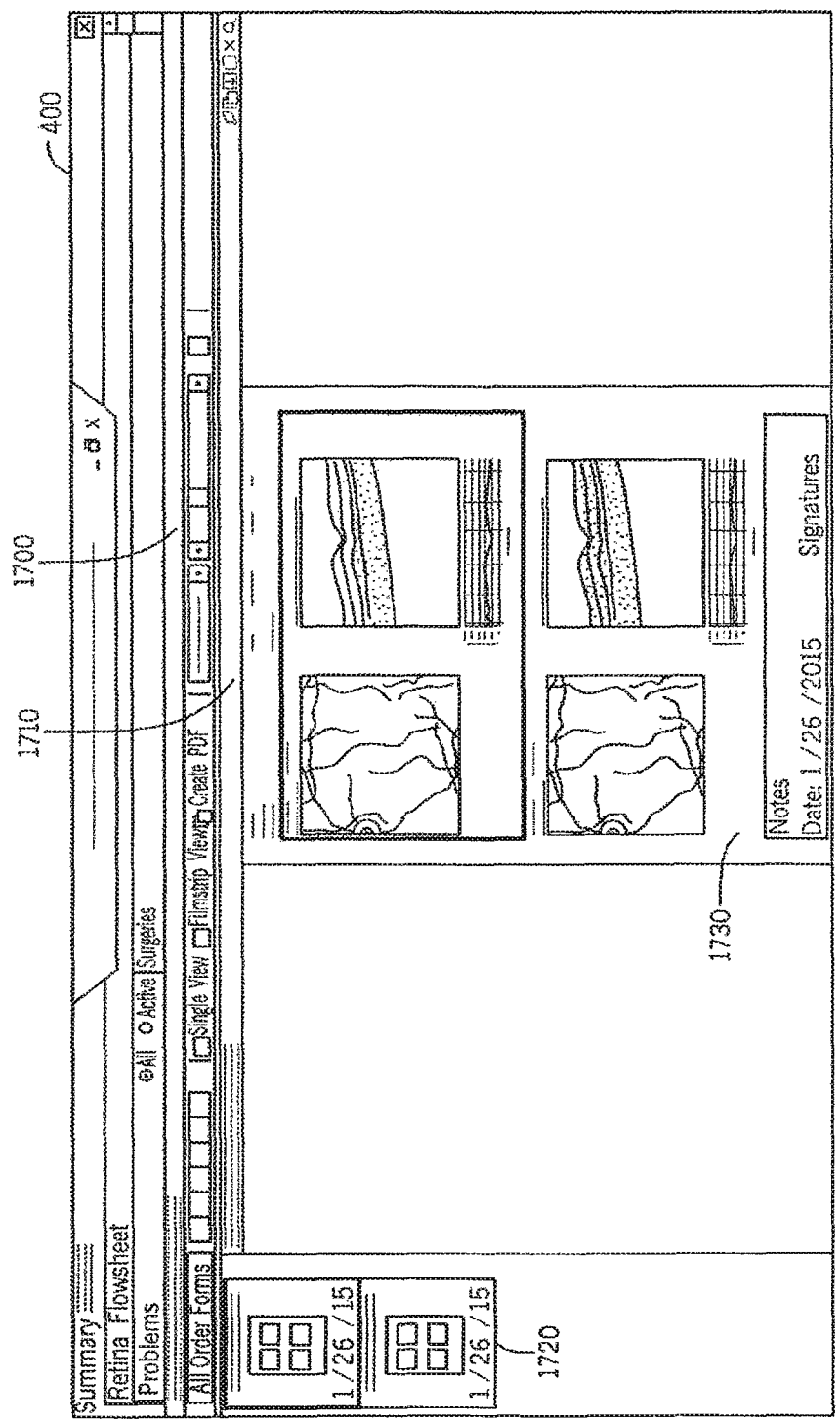
FIG. 7 illustrates a medical records access window in accordance with some embodiments of the invention.

As an example embodiment of the invention, the medical service tracking system and method can display at least one medical record as a result of the user action 887. For example, FIG. 7 illustrates a medical records access window 1700 in accordance with some embodiments of the invention. In some embodiments, the user's action (represented by user action 887) can direct the medical service tracking system and method to display the medical record access window 1700 including a medical record display 1710. Further, in some embodiments, at least one medical record 1730 can be selected from the medical record list 1720 for viewing in the medical record display 1710. As illustrated in FIG. 7, in some embodiments of the invention, the at least one medical record 1730 can include an image or photograph such as an optical and/or fluorescein angiogram image. In other embodiments, the at least one medical record 1730 can comprise an X-ray image. In some further embodiments, the at least one medical record 1730 can include an MRI scan or any report or anything ordered or performed by the doctors. In some embodiments, the at least one medical record 1730 can comprise one or more dictated letters from the user or another medical provider. Further, in some embodiments, the at least one medical record 1730 can comprise a record or any portion of a correspondence from another medical provider.

In some embodiments of the invention, the medical service tracking system and method can enable a user to access underlying information linked or related to diagnostic codes. In some other embodiments, the medical service tracking system and method can enable a user to access underlying information linked or related billing codes. For example, in some embodiments, using a single click or mouse-over, a user can use the medical tracking display window 500 of the medical record dashboard 400 to access and view any information related to diagnostic and/or billing codes. In some embodiments, the diagnostic and/or billing code information and payment history can be displayed in a separate document or window. In some other embodiments, diagnostic and/or billing code information can be display overlaid onto the medical record dashboard 400 (e.g., as a pop-up window or transient text and/or graphics).

In some embodiments, the at least one medical record 1730 can comprise a transition of care document (hereinafter "CCD"). In some embodiments of the invention, the medical services tracking system and method can be configured to receive one or more CCDs from one or more medical providers for display to the user. In some embodiments, medical services tracking system and method can be configured to extract information from the CCD for display to the user. For example, in some embodiments, information from a received CCD can be extracted and used to populate one or more data columns or fields of the medical record dashboard 400 and/or one or more linked data columns or fields of the medical record dashboard 400. In some other embodiments, the medical services tracking system and method, enabled by the system 30, can be configured to receive direct messaging information. The medical services tracking system and method can be configured with standards and profiles required for interoperability and document-based health information exchange with other healthcare organizations. These can include IHE profiles, CDA and CCD, NwHIN Direct, HL7v2, HL7v3, DICOM, X12, ITK (UK), DMP (France), and NEHTA (Australia), etc. For example, in some embodiments, the system 30 can include an HL7 message router and schemas for exchange of direct messages including a graphical editor for transforming messages and data.

Figure 8:
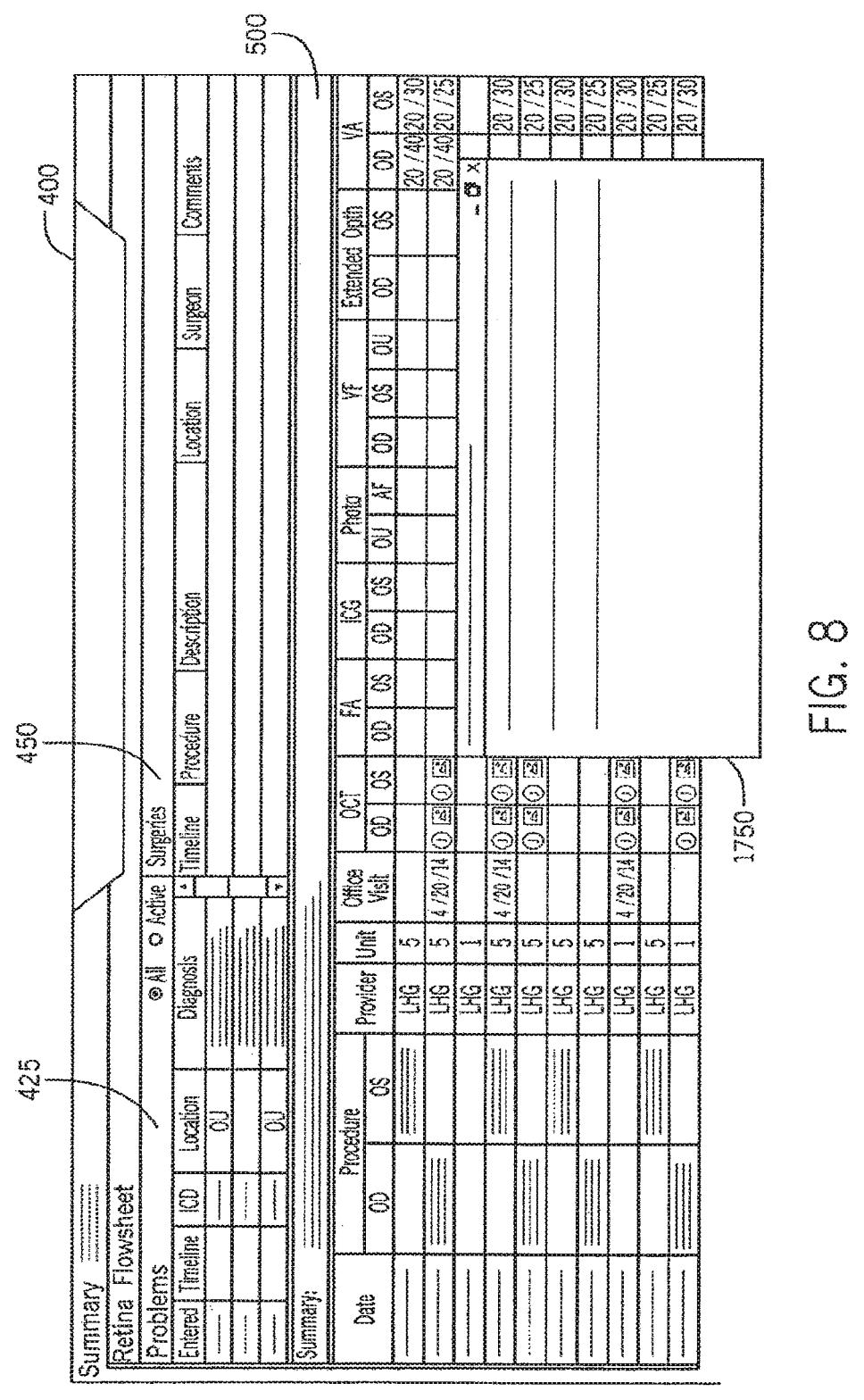

In some embodiments of the invention, the user can retrieve and/or update information related to a medical diagnosis. For example, FIG. 8 illustrates a medical record and diagnosis update process in accordance with some embodiments of the invention. In some embodiments, the medical record dashboard 400 including problems window 425, surgeries window 450, summary window 475, and medical tracking display window 500 can include an option to enable a user to update or enter at least one medical diagnosis using a medical record/diagnosis window 1750. In some embodiments, multiple medical diagnoses can be provided or updated by a user. In some embodiments, the user providing the medical diagnosis can be any medical practitioner providing the service or procedure to the patient. In some other embodiments, the medical record/diagnosis window 1750 can be updated by a user other than the medical practitioner providing the service or procedure to the patient.

Figure 9:
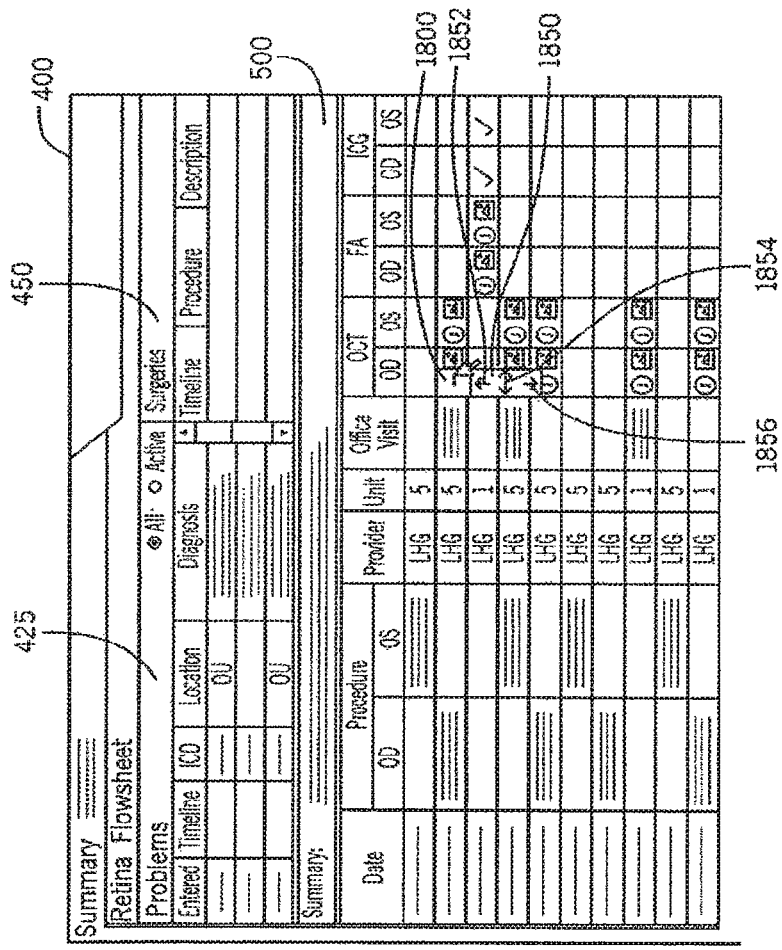
FIG. 9 illustrates a medical record update marker process in accordance with some embodiments of the invention.

In some embodiments, the medical services tracking system and method can enable a user to update information displayed in the medical tracking display window 500. For example, in some embodiments, a user can update information related to a medical diagnosis and/or information related to a medical test or other service or procedure. For example, FIG. 9 illustrates a medical record update marker process in accordance with some embodiments of the invention. The medical record dashboard 400, including problems window 425, surgeries window 450, and summary window 475 is shown with a record update marker 1800 being accessed by a user and displaying a update marker selection tab 1850. The update marker selection tab 1850 can include a user selectable marker or icon. For example, in some embodiments, update marker selection tab 1850 can include a selectable diagnosis indicator 1852, a selectable diagnosis indicator 1854, and/or a selectable diagnosis indicator 1856. In some embodiments, the selectable diagnosis indicators 1852, 1854, 1856 can provide a graphical representation of a medical diagnosis, outcome, or test. For example, in some embodiments, the diagnosis indicators 1852, 1854, 1886 can provide a visual representation of an improvement of a medical problem, disease, or symptom, or a worsening of a medical problem, disease, or symptom. Further, in some embodiments, the diagnosis indicators 1852, 1854, 1856 can provide a visual representation of a medical problem, disease, or symptom that is stable or substantially unchanged. In some embodiments, the diagnosis indicators 1852, 1854, 1856 can provide a visual representation directly related to one or more variables of a physical test. For example, in the field of ophthalmology, some imaging tests can provide an analysis of the thickness of the retina related to an eye disease such as macular degeneration. In some embodiments, an increase in thickness can represent a worsening of the condition, whereas a decrease in thickness can represent an improvement. A stable or unchanged thickness can indicate the disease is responding to treatment or is in remission.

Further, using a color change or other method (e.g., such as using italics, bold text, and/or underlined text), a particular important change in a test can be marked for internal reference alerting a doctor to the tests or procedures that are important and to take note for future reference. Further, in some embodiments, the diagnosis indicators 1852, 1854, 1856 can comprise a color and/or graphical change providing a visual representation of items billed, items not billed, or tests needing reports or interpretations are required. A color change or other method (e.g., such as using italics, bold text, and/or underlined text) can also tell a doctor if a test or procedure was billed, rejected, or if an interpretation needs to be made.

As an example embodiment, the diagnosis indicators 1852, 1854, 1856 can provide a visual representation of the status of a patient with an eye disease such as macular degeneration. For example, in some embodiments, the diagnosis indicators 1852, 1854, 1856 can be selected from the update marker selection tab 1850 when the user intends to indicate a worsening of the condition (e.g., where the thickness of the retina is increasing). In some embodiments, any of the diagnosis indicators 1852, 1854, 1856 can be color-coded to represent a status or provide a visual indicator of a medical condition, test, or diagnosis linked to the diagnosis indicators 1850. For example, in some embodiments, the diagnosis indicator 1852 can be color coded red and the diagnosis indicator 1856 can be color-coded green. Further, the diagnosis indicator 1854 can be color-coded blue or black. In some other embodiments, the diagnosis indicator 1852 can be color coded green and the diagnosis indicator 1856 can be color-coded red. In other embodiments, other graphical markers or icons can be used, and/or other colors can be used to differentiate the diagnosis indicators 1852, 1854, 1856. Further, in some embodiments, in addition to or in place of using a color differentiation between the diagnosis indicators 1852, 1854, 1856, one or more of the diagnosis indicators 1852, 1854, 1856 can flash or pulsate.

Figure 10A:
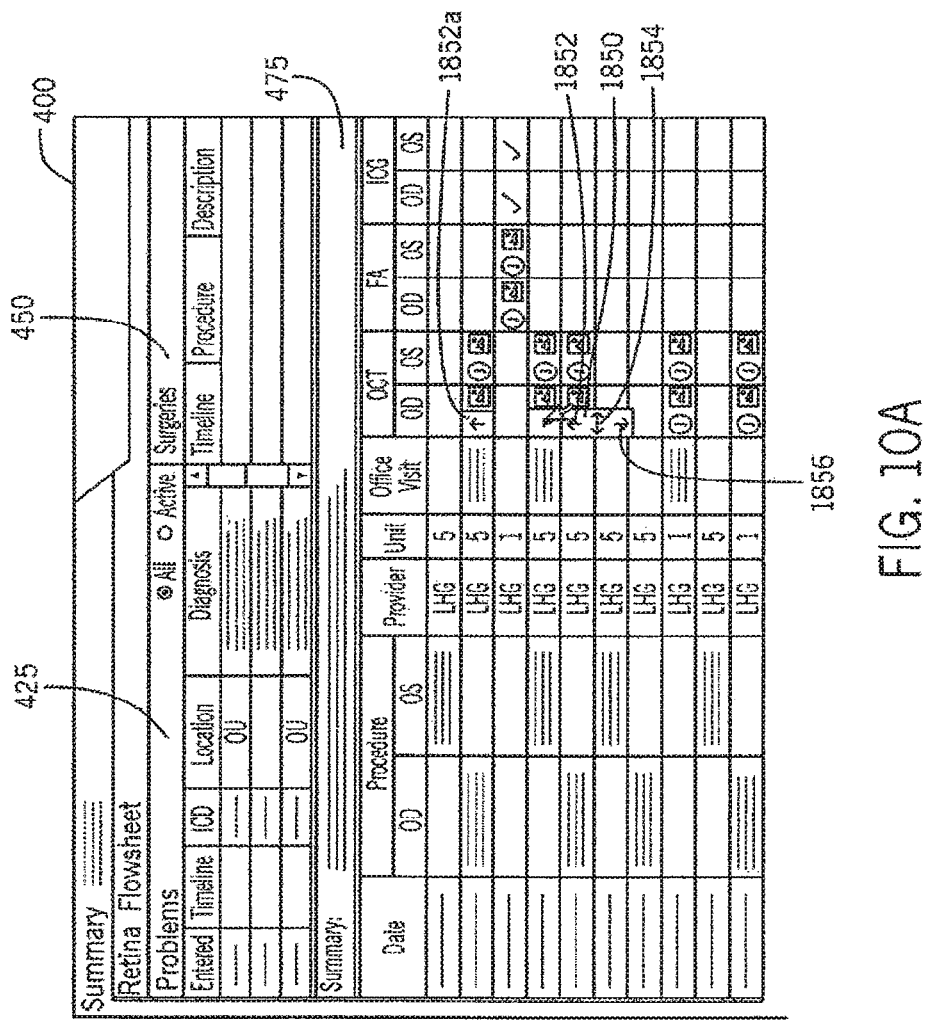
FIG. 10A illustrates a medical record update marker process in accordance with some embodiments of the invention.

In some embodiments, the medical services tracking system and method can enable a user to provide a plurality of updates to information displayed in the medical tracking display window 500. For example, in some embodiments, a user can update information related to a medical diagnosis and/or information related to a medical test or other service or procedure, and subsequently provide further updates to the same information or to other information. For example, FIG. 10A illustrates a medical record update marker process in accordance with some embodiments of the invention including medical record dashboard 400, with problems window 425, surgeries window 450, summary window 475, and medical tracking display window 500. The medical tracking display window 500 depicts diagnosis indicator 1852a representing previously updated information. The medical tracking display window 500 also illustrates a user updating information with a process described above using the update marker selection tab 1850 comprising a selection of diagnosis indicator 1852, diagnosis indicator 1854, or diagnosis indicator 1856.

Figure 10B:
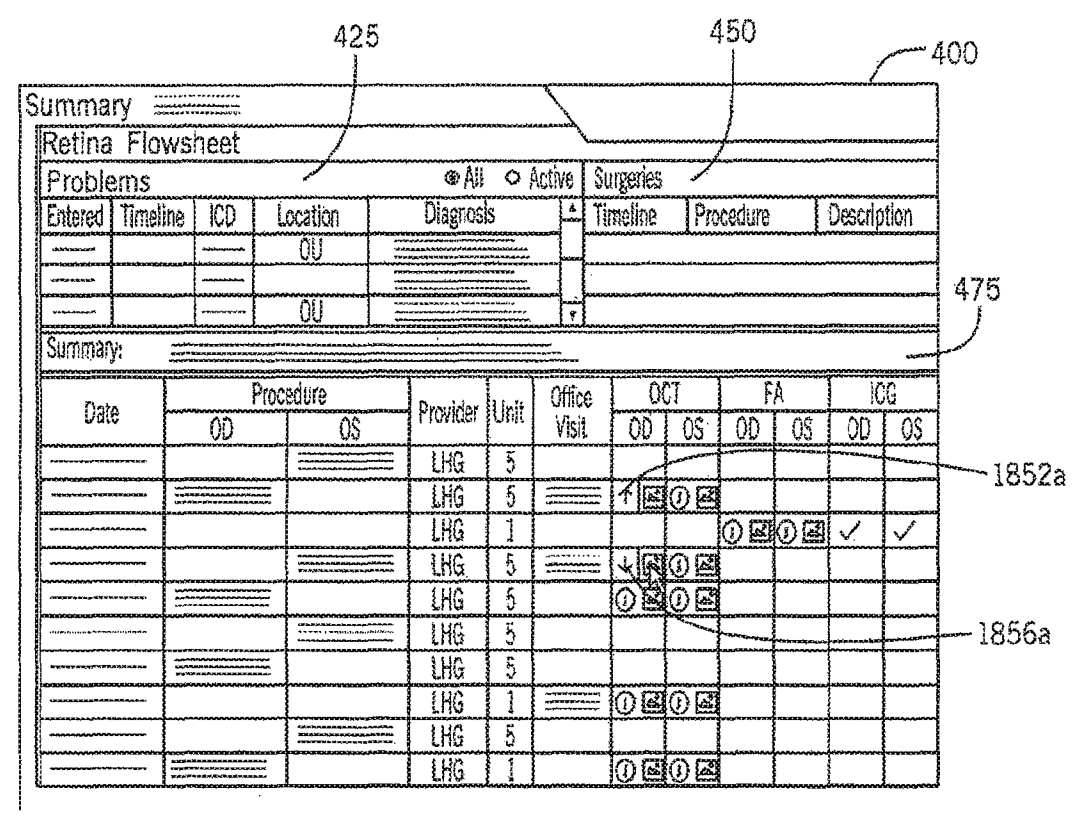

Further, FIG. 10B illustrates a medical record update marker process in accordance with some embodiments of the invention. Following the medical record update marker process shown in FIG. 10A, in some embodiments, the medical record dashboard 400 including medical record dashboard 400, with problems window 425, surgeries window 450, summary window 475, and medical tracking display window 500 can display diagnosis indicator 1852a and diagnosis indicator 1856a indicative of updated information or status of a patient and/or a patient's disease, test, or medical condition. Further, any ICD code can be inserted.

Figure 11:
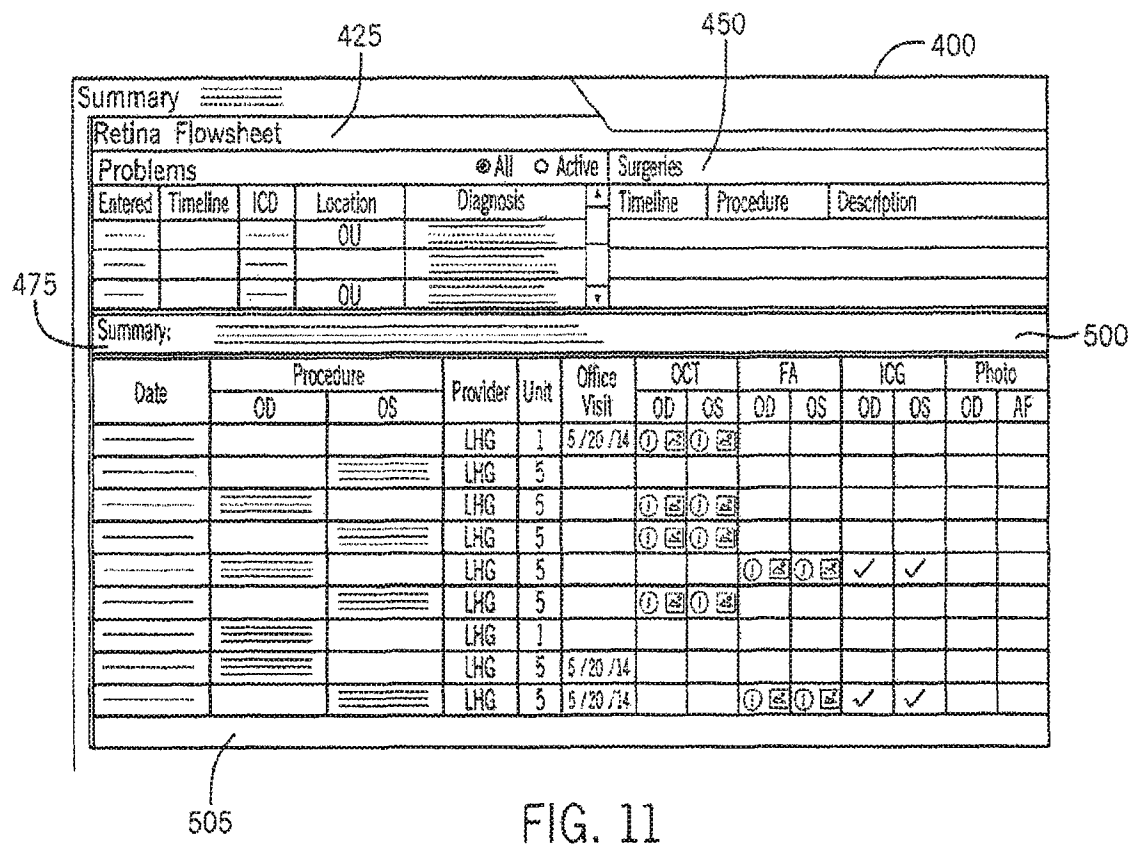

FIG. 11 illustrates a portion of the medical record dashboard 400 of FIG. 4A including a scrolled display in accordance with some embodiments of the invention. In some embodiments, the medical record dashboard 400 including problems window 425, surgeries window 450, summary window 475 can include a medical tracking display window 500 that comprises a scroll display 505. In some embodiments, any information displayed in the medical tracking display window 500 can be scrolled by the user to bring non-visible portions of the medical tracking display window 500 into view. This procedure can enable the user to view the entire history of the patient independent of the number of years of history that is on record.

Figure 12A:
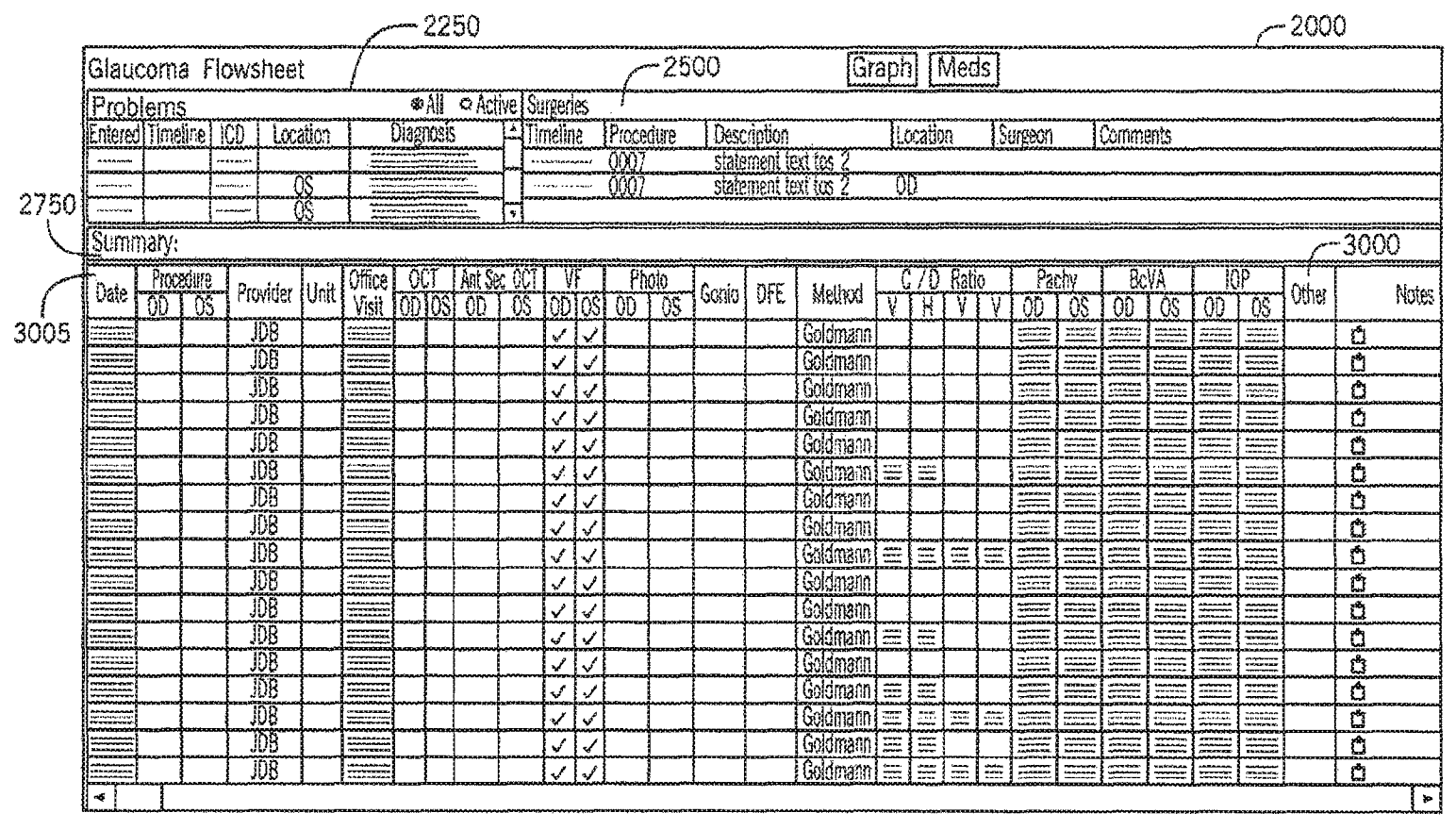

FIG. 12A illustrates a portion of the medical record dashboard 2000 in accordance with another embodiment of the invention. In some embodiments, the medical record dashboard 2000 can display data from one or more medical records, and/or track medical procedures and services based on claims made or billing signed off by a physician for one or more delivered medical procedures or services. Further, in some embodiments of the invention, the medical record dashboard 2000 can be auto-populated as a function of claims made or billing signed off by a physician, auto-populated from any portion of a selected chart. In this instance, any data displayed within the medical record dashboard 2000 can be derived from one or more claim records that have been billed for one or more procedures or services have previously been provided to the patient. In reference to the medical record dashboard 2000 and/or the previously described medical record dashboard 400, in some embodiments of the invention, auto-populating visits by actual claims made or billings signed off by a physician, by definition occurs after the visit with the patient. In some embodiments, the medical services tracking system and method can auto-populate the some information at the time the patient is seen, or shortly thereafter, or even before in preparation for a visit (i.e., lab results), so that even if a patient is not seen on a particular day, the user (e.g., medical provider) can view the displayed information in the table for information. For example, in some embodiments, information related to vision can be made with the current date at the time patient is seen. In some embodiments, a user or user's assistant can update the medical services tracking system and method with medical tests or test results (e.g., a vision test) as they are performed or shortly thereafter (i.e., on the same day). In this example, this information can immediately trigger the current date and auto-populate the vision column. This information can then be immediately viewed by a user and/or medical provider, and can be updated with notes or comments or other information as the user and/or medical provider is attending to the patient. Further, after the claim has been made for any diagnostic tests or examinations or procedures that have not yet been billed, the date will then auto-populate in the future with the other related columns. In some embodiments, while examining a patient, important information and/or certain parameters that are critical to follow can be immediately updated to the medical services tracking system and method. Using these procedures, the medical services tracking system and method can enable the medical provider to review the patient's medical history, treatment history, and instantly see items of importance on the day they're examining a patient. For example, the user and/or medical provider can be enabled by the medical services tracking system and method, on the day the patient is examined, to review information such as a vision or glaucoma table, intraocular pressure, blood pressure, blood sugar, etc. When billing claims are made, further information is filled to complete the billed claims record. As a further example, a patient may be seen a few days apart and the diagnostic tests etc. and claims have not yet been made, however the medical services tracking system and method can be configured to show that the patient was seen that day (e.g., with a vision, pressure test, etc.), and the medical services tracking system and method can enable a user (such as a physician) to interpret and/or add special notes on the day they see a patient or before they see the patient rather than waiting to make some notes when a claim is actually generated.

In some embodiments, the medical office wishes to communicate results or a test (e.g., a pathology result or test) a blinking cursor can appear to alert a lab physician to confirm done or other correspondence can be auto-populated into other portions of the EMR chart or table. This can allow the flow sheet to interact and auto-populate other sections of the EMR. Also any written or type correspondence or any links to dictated information using voice recognition coupled to or integrated with the medical services tracking system and method.

By following a patient on the day of delivery (e.g., for a vision intraocular pressure or anything else) can enable the user and/or medical provider to see the diagnostic test on same day even though it has not been billed. Further, this procedure can enable the medical provider to optionally add a note (as described earlier) and allow free hand typing at the end of the line.

In some embodiments, medical information populated within the medical services tracking system and method (e.g., shown as visual cues, icons, or markers 885 representing medical services, procedures or tests performed or provided to the patient) can include a visual marker such as a red dot. In some embodiments, the medical services tracking system and method can display the red dot until a claim is actually made at which time the medical services tracking system and method can display can display a green dot (i.e., the medical services tracking system and method can convert the red dot to a green dot). In some embodiments, by clicking on the dot, the user can toggle between the payment screen and the medical tracking display window 500, 3000. This can allow medical providers to improve patient care, to review the actual picture of a diagnostic test that is displayed within the medical tracking display window 500, 3000, to review other diagnostic tests results, and to compare to what happened on other days. In some embodiments, at any time, a medical provider can click on the dot to access a display where the claim is billed, and any payment that was made can be displayed. This process can help to reduce medical errors enable medical providers to quickly review the billings and claims made or billings signed off by a physician and payments portions of the medical services tracking system and method. Further, this procedure can serves as a double check to research out what actually happened in previous patient visits which will reduce medical errors and assist medical providers with deciding on future patient care.

In some embodiments, the medical record dashboard 2000 can display information related to medical procedures or services in relation to care of a patient with glaucoma. In some embodiments, the medical record dashboard 2000 can display various windows and sub-windows based on a user preference and/or current or previous user interaction with the medical record dashboard 2000. Some embodiments include a medical record dashboard 2000 that comprises information columns 2050 including a problems window 2250 and/or a surgeries window 2500 where information related to a patient's medical problems and surgeries can be displayed. In some embodiments, the medical record dashboard 2000 can include a summary window 2750 enabling a user to view and edit summary information related to the patient, any details of care provided to the patient, and/or and any medical diagnosis information prepared by a medical practitioner. Further, the medical record dashboard 2000 can also display detailed information related to any medical procedures or services provided to the patient, including procedures or services that are auto-populated by claims made or billing signed off by a physician as detailed above or other method. For example, in some embodiments, the medical record dashboard 2000 can display a medical tracking display window 3000 including a plurality of information columns 3005. In some embodiments, the medical tracking display window 3000 can be scrolled by the user to display other portions of the medical tracking display window 500.

In some embodiments, the medical record dashboards 400, 2000 can also display detailed information related to notification of payment of any medical procedures or services provided to the patient, including procedures or services that are auto-populated by claims made or billing signed off by a physician as detailed above or other method. Moreover, the medical record dashboards 400, 2000 can enable a user to access and/or track the status of the billing and payment process at any point in time. For example, in some embodiments, the medical record dashboards 400, 2000 can access and view any patient encounter form (i.e. a superbill), any claims made to a clearing house, any updates on accepted or rejected bills from the clearing house, any claims made to an insurance company, and/or any payments received for any claims made.

Figure 12B:
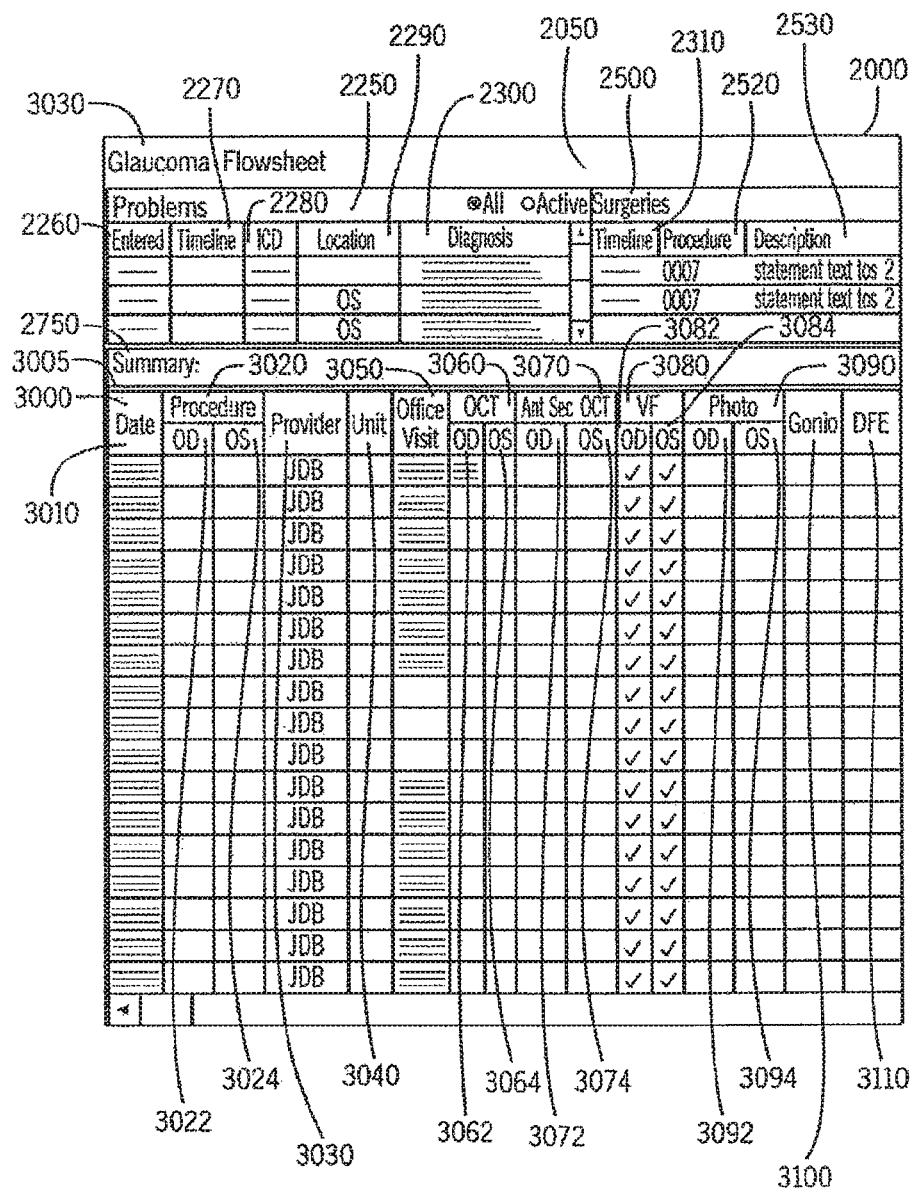
FIG. 12B illustrates a portion of the medical record dashboard of FIG. 12A in accordance with some embodiments of the invention.

FIG. 12B illustrates a portion of the medical record dashboard 2000 of FIG. 12A in accordance with some embodiments of the invention. As shown, the problems window 2250 can include a date and time information in entered date column 2260, a timeline column 2270, an "ICD" column 2280 for ICD code information, location of the problem or disorder (shown as "OD", "OS", "OU" identifying right eye, left eye, both eyes) (column 2290), and a diagnosis column 2300 for detailing information related to an initial diagnosis or final diagnosis of a patients problem or disorder. Further, the surgeries window 450 can include information related to services or procedures were provided to the patient (procedure columns 2520), a description of the services or procedures performed (description columns 2530), and when the services or procedures were provided to the patient (shown as timeline columns 2310), and can include a surgical report that can be brought up and viewed by the user.

Referring to the medical tracking display window 3000, the information columns 3005 can include a date column 3010, and a procedure column 3020 illustrating or providing access to information detailing one or more procedures performed on the patient. Further, the procedure column 3020 can include an "OD" column 3022, and "OS" column 3024 providing right and left eye procedure information. In some embodiments, information related to the medical provider, location where the procedure was performed, and office visit information can be provided to the user in the provider column 3030, and unit column 3040, and office visit column 3050.

In some embodiments of the invention, the medical tracking display window 3000 can enable a user to view information related to tests and procedures performed on the patient including, but not limited to one or more medical imaging procedures such as an optical coherence tomography ("OCT"), or fluorescein angiography ("FA"), and/or indocyanine green chorioangiography ("ICG"). In some embodiments, medical procedures performed (including any of the aforementioned medical imaging procedures) that have been billed and claimed can be viewed or accessed by a user within any of the "OCT" column 3060 (shown split as an "OD" column 3062 and "OS" column 3064), an "Ant Seg OCT" column 3070 (split as an "OD" column 3072 and "OS" column 3074).

In some embodiments, if visual function tests were performed, information can be viewed or accessed in the "VF" column 3080 (including an "OD" column 3082, and/or an "OS" column 3084. Some embodiments include a photo column 3090 configured to enable a user to access any photographic images of the patients eyes including optical and/or auto-fluorescent images of the eyes ("OD" column 3092 and "OS" column 3094). Further, some embodiments include a Gonio column 3100 providing access to gonioscopy data and/or information related to a dilated fundus examination ("DFE" column 3110). In some embodiments, the surgeries window 2500, can include location column 2540, surgeon column 2550, and a comments column 2560 (shown in FIG. 12C).

Figure 12C:
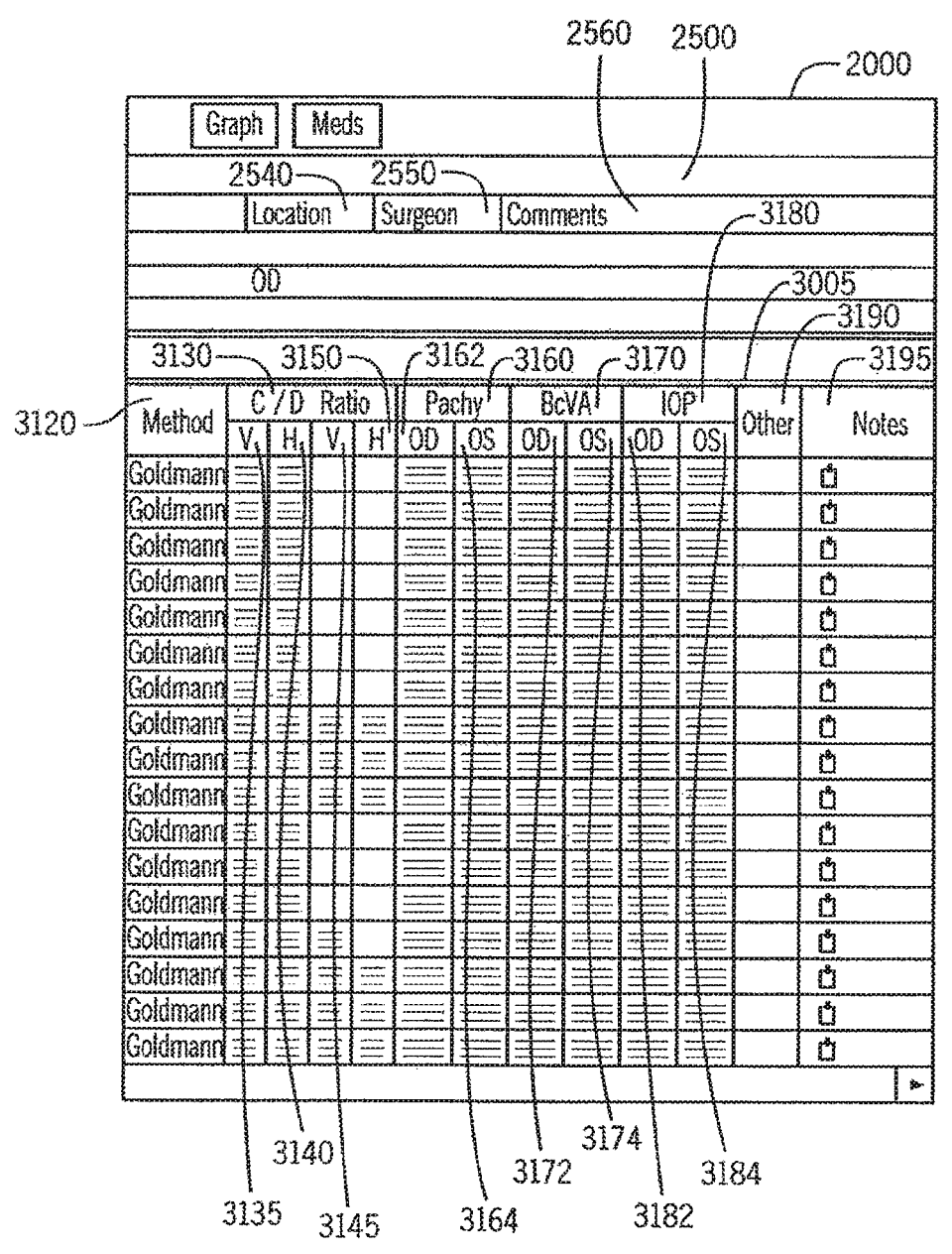

In some embodiments of the invention, the medical tracking display window 3000 can enable a user to view information related to tests and procedures performed on the patient including a cup-to-disc ratio ("C/D") to assess the progression of glaucoma, Pachymetry data ("Pachy"), refraction test information such as best-corrected visual acuity ("BCVA"), and/or intraocular pressure (IOP) data. For example, FIG. 12C illustrates a portion of the medical record dashboard of FIG. 12A in accordance with some embodiments of the invention and shows method column 3120, "C/D ratio" column 3130, "Pachy" columns 3160, "BcVA" columns 3170, and "IOP" columns 3180. In some embodiments, the "C/D ratio" column 3130 includes "V" column 3135, "H" column 3140, "V" column 3150, and "H" column 3150. Further, in some embodiments, the "Pachy" columns 3160 includes "OD" column 3162, and "OS" column 3164. In some embodiments, the "BcVA" columns 3170 includes "OD" columns 3172, and "OS" columns 3174. Some embodiments include "IOP" columns 3180 including "OD" columns 3182, and "OS" columns 3184. In some embodiments, other columns 3190 can be used to add additional test information. Further, the medical tracking display window 3000 can also include a notes column 3195 for accessing and updating notes related to tests and medical diagnosis. In some embodiments, the tracking display window 3000 can be updated with comments and notes as described earlier with respect to tracking display window 400.

In some embodiments of the invention, the medical services tracking system and method can display and auto-populate the medical record dashboard 400 and/or the medical record dashboard 2000 with more than one patient information. For example, in some embodiments, any windows, sections, or columns of the medical record dashboard 400, 2000 can display information related to a plurality of patients.

Further, in some embodiments of the invention, any information displayed by the medical services tracking system and method can display and auto-populate the medical record dashboard 400 and/or the medical record dashboard 2000 as a function of patients seen during a specified time period. In some other embodiments of the invention, the medical services tracking system and method can display and auto-populate the medical record dashboard 400 and/or the medical record dashboard 2000 as a function of a specified disease and/or diagnosis. For example, in some embodiments, the medical services tracking system and method can display and auto-populate the medical record dashboard 400 and/or the medical record dashboard 2000 as a function of a CPT code or ICD code from input received from a physician or other medical practitioner or provider. For instance, every patient who has the diagnosis of diabetes with their name and the date last scene is auto-populated. Certain parameters that may need to be followed by the user from all of their patients with this condition can be auto-populated. For example, in the case of patients with diabetes, parameters can include how often they've missed appointments, blood sugar, hemoglobin A-1 C, medications, major new medical complications such as heart attack, stroke, amputations, blindness, each of which can be auto populated and followed to enable the user to see how all their patients are doing. In some embodiments, the user can also receive a daily report on all the patients they've seen, what the diagnosis codes are and what CPT, ICD, or office visit billing codes were done. In some embodiments, any report or diagnostic test can be sent to a patient portal, to an email server, and/or as a fax. Further, the user can be alerted when the claims go out and when they're actually paid. For example, in some embodiments, the above described methods of display can provide a mechanism for determining payments to the user, and if claims are being made for each patient seen in any particular day, week or month.

Examples of the aforementioned examples of displayed data sorted and viewable by patient, disease time period, physician, etc., are shown in FIGS. 12D and 12E. For example, FIG. 12D illustrates a portion of a medical record dashboard 3200 for display as a function of disease or patient in accordance with some embodiments of the invention. Further, FIG. 12E illustrates a portion of a medical record dashboard 3600 for display as a function of patients or physician or disease state in accordance with some embodiments of the invention. In some embodiments, the medical record dashboards 3200, 3600 can be displayed overlaid on a previously viewed dashboard such as medical record dashboard 400, 2000. For example, in some embodiments, the medical record dashboards 3200, 3600 can be displayed in the medical tracking display window 500. In other embodiments, the medical record dashboards 3200, 3600 can be displayed independently from the medical record dashboard 400, 2000, and the user can toggle a display of any of the medical record dashboard 400, 2000, 3200, 3600.

Referring to FIG. 12D, including providing a list of patients 3205, within column 3210, an entire day of patients listed by date can be provided or the list can comprise a single patient with multiple visits. Within column 3220, an office visit and any items billed for a routine examination day and any other CPT codes billed that day can be displayed. Some specialties will have many CPT codes during an office visit (e.g. Ophthalmologists, whereas others (e.g., Gastroenterologists) may have four during an office visit. Column 3230 can include the procedures that a physician may perform, and are usually not on the same day as the exam (these are GI doctors examples). Column 3240 can include various important parameters that can be followed for a specific patient. Column 3250 includes where a doctor writes notes about patient care issues. Column 3260 can takes the user to that patient's personal EMR or review table and can also send a message to the patient. Column 3270 can takes the physician to the charge payment history of the patient, and also a message can be sent to the billing department from this table. In some embodiments, columns 3220, 3230 can be colored 'black' when a claim is made, and can be colored 'green' if paid, and can be colored 'yellow' if a payment is pending, and can be colored 'red' if payment denied by one rendition.

Referring to FIG. 12E, including example embodiments related to patients with diabetes, the display for patients 3610 can include can include a variety of medical, billing, and insurance related information. This medical record dashboard 3600 can be display as shown, or can be sorted based on any of the data columns. For example, the patients 3610 can be shown including information displaying insurance coverage 3620, date of diagnosis of diabetes 3630, the patient's age 3640, the patient's weight 3650, the patient's height 3660, their body mass index 3670, their initial presenting HbgA1C 3680, their most recent HbgA1C 3690, their hypertension status 3692, their recent blood pressure 3694, their All ICD diagnosis 3696 and their current or past medications 3698. In some embodiments, the medical record dashboard 3600 can be reconfigured to shown patients 3610 sorted by any of the columns 3620, 3630, 3640, 3650, 3660, 3670, 3680, 3690, 3692, 3694, 3696, 3698.

In some embodiments of the invention, the medical services tracking system and method can enable a user to update a medical record dashboard 400 and/or the medical record dashboard 2000 to be mark personalized to the next treating physician or patient to follow progression changed outcomes. This will be used to access quality of care and prove effectiveness and results resolution, and can be used for negotiating with insurance carriers or for performance research. For example, anything can be tracked or personalized to the needs of the treating physician or patient to follow progression, changes, and outcomes. This can be used to assess quality of care and prove effectiveness and results of treatment. Quality outcome measures are critical for all practices to start to follow as this improves patient care, and in the future, a physician's financial compensation from insurance companies, or any penalization will be determined based on the quality of care metric. Further, physicians who participate in clinical research must follow defined parameters over time as they learn whether a particular drug, or device, or other item being investigated actually improve changes or worsens particular parameters. By way of example in FIG. 4C, 1100 vision is followed, and other column 1200, many different parameters that may change over time can be added. For example, as described earlier with respect to participation in clinical research studies, other factors followed such as central macular thickness ("CMT"), or ischemic index ("ISI") (% and A scan in millimeters) can be followed. Therefore, every time the patient comes in to be examined, the table can serve the multi-purpose of treating the patient, and for inputting research data from the office visit right into the table. This can then auto-populate into another portion of the EMR or derive these numerical values and place them into the research Excel spreadsheet. Also it could go the other way, where if the Excel research spreadsheet can be also have the data inputted into the review table.

In some embodiments of the invention, the medical services tracking system and method can enable a date alert or self-destruction of any information or data entered or auto-populated in the medical record dashboard 400 and/or the medical record dashboard 2000. For example, in some embodiments, any message, or note, or summary, or any medical data can include a date alert and/or a self-destruct function that can instruct the medical services tracking system and method to remove and/or delete information from the medical record dashboard 400 and/or the medical record dashboard 2000. In other embodiments, the historical date and/or an alert or warning can be provided with any auto-populated or user-summoned information to assist the user with an assignment of relevancy to any data being reviewed prior to, during, or after a patient visit or examination. In some embodiments, this feature can optimize the standard of care being delivered by the user. For instance, this feature can help monitor preferred practice patterns or serve as a reminder on information needed for clinical review.

Figure 13:
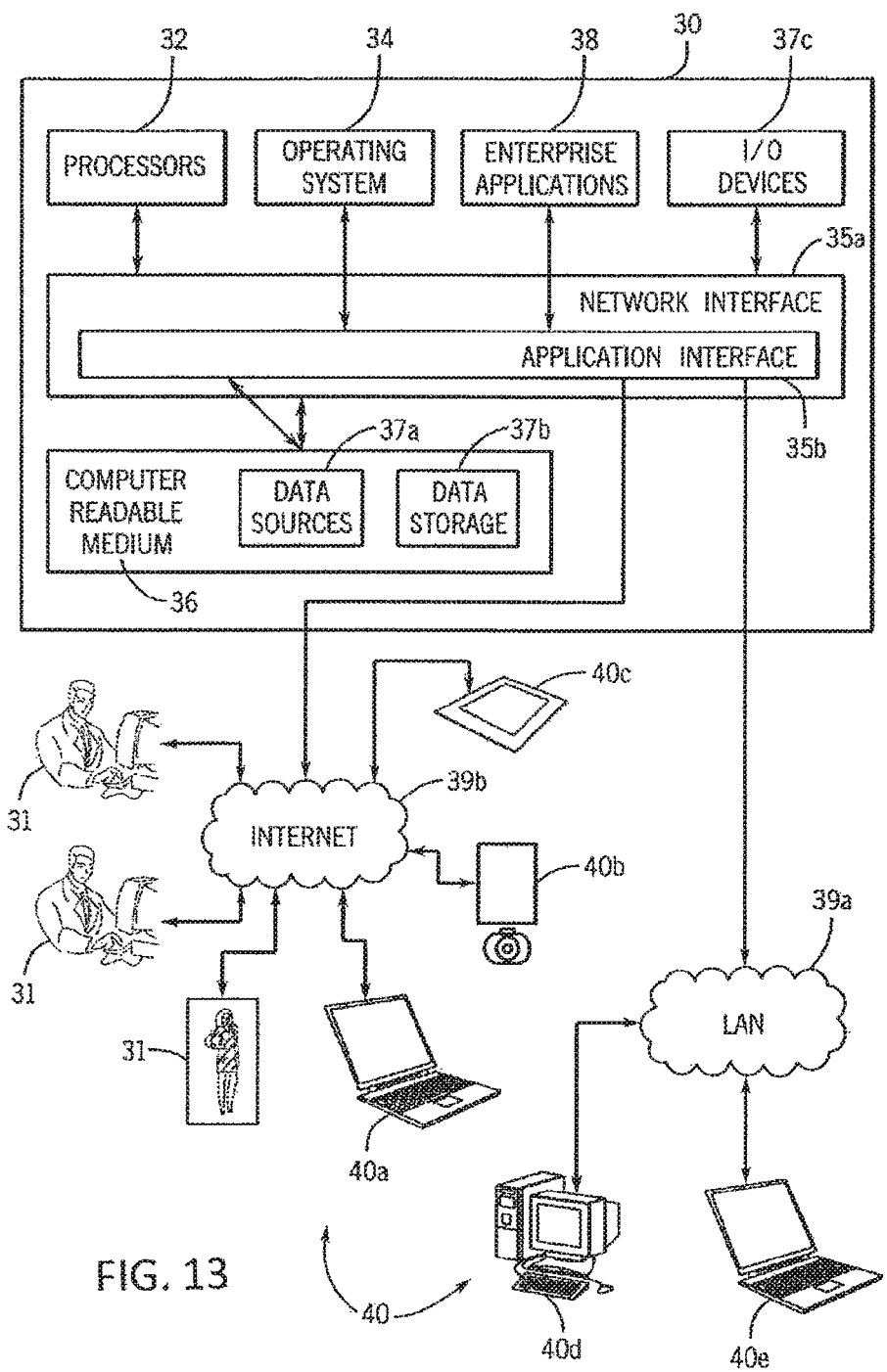
FIG. 13 illustrates a computer system configured for operating and processing components of the medical services tracking system and method in accordance with some embodiments of the invention.

FIG. 13 illustrates a computer system 30 configured for operating and processing components of the medical services tracking system and method in accordance with some embodiments of the invention. In some embodiments, the computer system 30 can process one or more software modules of the aforementioned medical services tracking system and method and display information related to medical services within at least one graphical user interface. Further, in some embodiments, using the computer system 30, the medical services tracking system and method can manage the organization of data and data flow between the various components of the medical services tracking system and method. For example, in some embodiments, the computer system 30 can be configured to process and display the medical record dashboard 400 and/or the medical record dashboard 2000. Further, in some embodiments, the computer system 30 can be configured to process and display auto-populated data within any portion of the medical record dashboards 400, 2000, including, but not limited to the medical tracking display window 500 and/or the medical tracking display window 3000.

In some embodiments, the system 30 can include at least one computing device, including one or more processors 32. Some processors 32 can include processors 32 residing in one or more conventional server platforms. The system 30 can include a network interface 35a and an application interface 35b coupled to at least one processors 32 capable of running at least one operating system 34. Further, the system 30 can include a network interface 35a and an application interface 35b coupled to at least one processors 32 capable of running one or more of the software modules (e.g., enterprise applications 38). Some embodiments of the invention also relate to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data are obtained over a network the data can be processed by other computers on the network, e.g. a cloud of computing resources.

With the above embodiments in mind, it should be understood that the invention can employ various computer-implemented operations involving medical services tracking data stored in computer systems. Moreover, the above-described databases and models throughout the medical services tracking can store analytical models and other data on computer-readable storage media within the system 30 and on computer-readable storage media coupled to the system 30. In addition, the above-described applications of the medical services tracking system can be stored on computer-readable storage media within the system 30 and on computer-readable storage media coupled to the system 30. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Some embodiments include the system 30 comprising at least one computer readable medium 36 coupled to at least one data storage device 37b, and/or at least one data source 37a, and/or at least one input/output device 37c. In some embodiments, the invention embodied by the medical services tracking system can also be embodied as computer readable code on a computer readable medium 36. The computer readable medium 36 can be any data storage device that can store data, which can thereafter be read by a computer system (such as the system 30). Examples of the computer readable medium 36 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 32).

In some embodiments of the invention, the computer readable medium 36 can also be distributed over a conventional computer network via the network interface 35a so that the medical services tracking system embodied by the computer readable code can be stored and executed in a distributed fashion. For example, in some embodiments, one or more components of the system 30 can be tethered to send and/or receive data through a local area network ("LAN") 39a. In some further embodiments, one or more components of the system 30 can be tethered to send or receive data through an internet 39b (e.g., a wireless internet). In some embodiments, at least one software application 38 running on one or more processors 32 can be configured to be coupled for communication over a network 39a, 39b. In some embodiments, one or more components of the network 39a, 39b can include one or more resources for data storage, including any other form of computer readable media beyond the media 36 for storing information and including any form of computer readable media for communicating information from one electronic device to another electronic device.

In some embodiments, the network 39a, 39b can include wide area networks ("WAN"), direct connections (e.g., through a universal serial bus port) or other forms of computer-readable media 36, or any combination thereof. Further, in some embodiments, one or more components of the network 39a, 39b can include a number of client devices which can be personal computers 40 including for example desktop computers 40d, laptop computers 40a, 40e, digital assistants and/or personal digital assistants (shown as 40c), cellular phones or mobile phones or smart phones (shown as 40b), pagers, digital tablets, internet appliances, and other processor-based devices. In general, a client device can be any type of external or internal devices such as a mouse, a CD-ROM, DVD, a keyboard, a display, or other input or output devices 37c. In some embodiments, various other forms of computer-readable media 36 can transmit or carry instructions to a computer 40, including a router, private or public network, or other transmission device or channel, both wired and wireless. The software modules 38 can be configured to send and receive data from a database (e.g., from a computer readable medium 36 including data sources 37a and data storage 37b that can comprise a database), and data can be received by the software modules 38 from at least one other source. For example, as described earlier, in some embodiments of the invention, using the system 30, the medical services tracking system and method can be configured to receive one or more CCD from one or more medical providers for display to the user 31. Further, in some embodiments, patient data can be retrieved from one or more master patient index databases (e.g. a master patient database managed by a government entity and/or a third party provider such as insurance company or collective of insurance companies). In some further embodiments, data can be retrieved from the national register of drugs and pharmaceuticals.

In some embodiments, at least one of the software modules 38 can be configured within the system 30 to output data to at least one user 31 via at least one digital display (e.g., to a computer 40 comprising a digital display). In some embodiments, the system 30 as described can enable one or more users 31 to receive, analyze, input, modify, create and send data to and from the system 30, including to and from one or more enterprise applications 38 running on the system 30. Some embodiments include at least one user 31 coupled to a computer 40 accessing one or more modules of the medical services tracking system including at least one enterprise applications 38 via a stationary I/O device 37c through a LAN 39a. In some other embodiments, the system 30 can enable at least one user 31 (through computer 40) accessing enterprise applications 38 via a stationary or mobile I/O device 37c through an internet 39a.

In some embodiments, the software modules 38 can include a server-based software platform that can include medical services tracking software modules suitable for hosting at least one user 31 account and at least one patient account or record. Further, some embodiments of invention includes the software modules 38 that can include at least one server-based software platform that can include medical services tracking software modules suitable for hosting at least at least one patient account or record. In some embodiments, using the system 30, the medical services tracking system and method can manage multiple user accounts and/or multiple patient accounts. In some embodiments, the software modules 38 can include a server-based software platform that can include medical services tracking software modules suitable for hosting a plurality of user accounts accessible by multiple medical practitioners (e.g., doctors, physicians, surgeons, optometrists, ophthalmologists, podiatrists, dentists, etc.) In some embodiments of the invention, patient accounts can be accessible by the patient's medical practitioner and not shared with other medical practitioners holding one or more user accounts within the medical services tracking system and method. In some further embodiments, one or more patient accounts can be accessible and shared by a user 31 associated with the patient account. For example, in some embodiments, a user 31 can grant access to at least one other user of the medical services tracking system and method. In some embodiments, shared access can be at least partially restricted. For example, in some embodiments, shared access can be restricted to viewing at least a portion of the shared patient's account or record.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examplesH the invention is not necessarily so limited, and that numerous other embodiments, examples, uses, modifications and departures from the embodiments, examples and uses are intended to be encompassed by the claims attached hereto. Various features and advantages of the invention are set forth in the following claims.

The invention claimed is:

1. A system for aggregating and tracking medical delivery to a patient comprising:
   a non-transitory computer-readable medium in data communication with at least one processor, the non-transitory computer-readable medium including software instructions comprising a medical services tracking system;

one or more processors configured to execute the software instructions to:

link to and receive patient related information from at least one patient database or server;

display at least one medical record dashboard comprising one or more windows concurrently viewable on a single screen, the one or more windows comprising at least one data entry field for displaying information received or derived from the at least one patient database or server;

auto-populate at least one of the at least one data entry field based at least in part on information associated with at least one of at least one unbilled claim and an unbilled bill signed off by a medical provider;

generate at least one icon representative of at least a portion of information in at least one of the at least one data entry field;

using the at least one generated icon to link to patient related information, via at least one of the one or more windows of the medical record dashboard, to enable entry of patient related information into at least one of the at least one data entry field; and display at least one of the at least one generated icon in the at least one data entry field for which the at least one icon was generated to provide at least one of a visual representation of patient related information and a link to patient related information in the at least one data entry field.

2. The system of claim 1, wherein the one or more processors are configured to dynamically link to at least one electronic medical records system.

3. The system of claim 2, wherein the one or more processors are configured to:

launch the medical services tracking system from a user interface of the electronic medical records system.

4. The system of claim 1, wherein the one or more processors are configured to:

switch between at least one display generated by the medical services tracking system and one or more displays generated by the electronic medical records system.

5. The system of claim 1, wherein the one or more processors are configured to:

provide a user edit access to the at least one data entry field to update or mark at least one data entry field.

6. The system of claim 5, wherein the update or mark comprises at least one icon, the icon representative of at least one of a worsening, a stable, or an improving medical symptom, medical condition, problem, disease or diagnostic test result.

7. The system of claim 1, wherein the at least one icon comprises a visual representation of financial data including at least one of items paid, items not paid, or items partially paid.

8. The system of claim 1, wherein the one or more processors are configured to provide, on the at least one medical record dashboard, at least one user-selectable link to a medical record, wherein the medical record is displayed without leaving a display of the at least one medical record dashboard.

9. The system of claim 8, wherein the at the at least one user-selectable medical record comprises at least one test result or diagnosis from any procedural terminology code or any international classification of disease codes.

10. The system of claim 1, wherein the at least one patient database comprises patient information from at least one of a medical provider, a transition of care document or proactive care form, or a direct message.

11. A method for aggregating and tracking medical delivery to a patient, comprising:

retrieving patient related information from at least one patient database or server;

displaying at least one medical record dashboard comprising one or more windows concurrently viewable on a single screen, the one or more windows comprising at least one data entry field for displaying information retrieved from or derived from the at least one patient database or server;

auto-populating at least one of the at least one data entry field based at least in part on information associated with at least one of at least one unbilled claim and an unbilled bill signed off by a medical provider;

generating at least one icon representative of at least a portion of information to be displayed in at least one of the at least one data entry field;

using the at least one generated icon to link to patient related information, via at least one of the one or more windows of the medical record dashboard, to enable entry of patient related information into at least one of the at least one data entry field; and displaying at least one of the at least one generated icon in the at least one data entry field for which the at least one icon was generated to provide at least one of a visual representation of patient related information and a link to patient related information in the at least one data entry field.

12. The method of claim 11, further comprising:

providing a user edit access to the at least one data entry field to update or mark at least one data entry field based on at least one medical diagnosis.

13. The method of claim 12, wherein the update or mark comprises at least one icon, the at least one icon representative of at least one of a worsening, a stable, or an improving medical symptom, medical condition, problem, disease or diagnostic test result.

14. The method of claim 11, wherein the at least one icon comprises a color or graphical change providing a visual representation of financial data including items paid, items not paid, and items partially paid.

15. The method of claim 11, further comprising:

providing, on the at least one medical record dashboard, at least one user-selectable link to a medical record.

16. The method of claim 11, wherein the at least one patient database or server comprises patient information from at least one of a medical provider, a transition of care document, a proactive care form, or a direct message.

17. The method of claim 15, wherein the at least one user-selectable medical record is displayed without leaving a display of the at least one medical record dashboard and the at the at least one user-selectable medical record comprises at least one test result or diagnosis from any procedural terminology code or any international classification of disease codes.

18. The system of claim 1, wherein the information received or derived from the at least one patient database or server is organized by rows or columns in the at least one medical record dashboard according to a date of service.

19. The system of claim 1, wherein the information received or derived from the at least one patient database comprises at least two of procedures, symptoms or clinical findings, or diagnostic test or laboratory results associated with a respective patient.

20. The system of claim 19, wherein the symptoms or clinical findings comprise at least one of visual acuity (VA), intra-ocular pressure (IOP), photograph, visual field, fluorescein angiography or optical coherence tomography (OCT).

21. The system of claim 1, wherein different colors or different graphical representations of that at least one icon are used to differentiate between different statuses of the information to be represented by the at least one icon.

22. The method of claim 11, wherein the information retrieved or derived from the at least one patient database or server is organized by rows or columns in the at least one medical record dashboard according to a date of service.

23. The method of claim 11, wherein the information received or derived from the at least one patient database comprises at least two of procedures, symptoms or clinical findings, or diagnostic test or laboratory results associated with a respective patient.

24. The method of claim 23, wherein the symptoms or clinical findings comprise at least one of visual acuity (VA), intra-ocular pressure (IOP), photograph, visual field, fluorescein angiography or optical coherence tomography (OCT).

25. The method of claim 11, wherein different colors or different graphical representations of that at least one icon are used to differentiate between different statuses of the information to be represented by the at least one icon.

26. The system of claim 1, wherein at least a portion of the patient related information, linked to using the at least one generated icon, is auto-populated into at least one of the at least one data entry field.

27. The method of claim 11, wherein at least a portion of the patient related information, linked to using the at least one generated icon, is auto-populated into at least one of the at least one data entry field.

* * * * *